United States Patent
Masao et al.

(10) Patent No.: US 6,294,758 B1
(45) Date of Patent: Sep. 25, 2001

(54) HEAT RADIATOR

(75) Inventors: Shiotani Masao; Hiroi Kazunori; Haraga Hisato; Fukushima Takenori; Kataoka Yumiko; Tanaka Shingo; Tsuboi Hiroshi; Ando Shigeru, all of Kitakyushu (JP)

(73) Assignee: Toto Ltd, Fukuoka-Ken (JP)

( * ) Notice: Subject to any disclaimer, the term of this patent is extended or adjusted under 35 U.S.C. 154(b) by 0 days.

(21) Appl. No.: 09/601,105

(22) PCT Filed: Jan. 27, 1999

(86) PCT No.: PCT/JP99/00320
§ 371 Date: Jul. 27, 2000
§ 102(e) Date: Jul. 27, 2000

(87) PCT Pub. No.: WO99/38429
PCT Pub. Date: Aug. 5, 1999

(30) Foreign Application Priority Data

| Jan. 28, 1998 | (JP) | 10-030455 |
|---|---|---|
| Feb. 27, 1998 | (JP) | 10-064813 |
| Apr. 20, 1998 | (JP) | 10-125260 |
| Jun. 19, 1998 | (JP) | 10-189879 |
| Jul. 6, 1998 | (JP) | 10-205835 |
| Jul. 21, 1998 | (JP) | 10-221044 |
| Aug. 6, 1998 | (JP) | 10-235020 |
| Aug. 6, 1998 | (JP) | 10-235022 |

(51) Int. Cl.[7] .............. H05B 1/00; H05B 3/00; H05B 11/00

(52) U.S. Cl. ............... 219/217; 219/527; 219/553; 607/100; 607/96; 392/435

(58) Field of Search ............ 4/237; 5/713; 219/217, 219/543, 213, 522, 553, 544, 548; 392/432, 435

(56) References Cited

U.S. PATENT DOCUMENTS

| 3,564,207 | * | 2/1971 | Joeckel | 219/544 |
|---|---|---|---|---|
| 3,805,024 | * | 4/1974 | Joeckel et al. | 219/553 |
| 3,878,361 | * | 4/1975 | Levin et al. | 219/522 |
| 3,961,157 | * | 6/1976 | Miller et al. | 392/435 |
| 3,968,344 | * | 7/1976 | Gallegos, Sr. | 219/217 |
| 4,303,074 | * | 12/1981 | Bender | 607/96 |
| 4,703,154 | * | 10/1987 | Ikegami et al. | 392/435 |
| 4,825,868 | * | 5/1989 | Susa et al. | 607/100 |
| 5,010,234 | * | 4/1991 | Scherrer et al. | 219/213 |
| 5,095,555 | * | 3/1992 | Torii et al. | 4/237 |
| 5,780,820 | * | 7/1998 | Komyoji et al. | 219/543 |

(List continued on next page.)

FOREIGN PATENT DOCUMENTS

| 63-32888 | 2/1978 | (JP) . |
|---|---|---|
| 59-191998 | 12/1984 | (JP) . |
| 60-170992 | 11/1985 | (JP) . |
| 60-170992 U | 11/1985 | (JP) . |
| 5-47456 | 2/1993 | (JP) . |
| 6-15595 | 4/1994 | (JP) . |
| 8-273810 | 10/1996 | (JP) . |
| 8-273810 A | 10/1996 | (JP) . |
| 9-140632 | 6/1997 | (JP) . |
| 9-23889 | 9/1997 | (JP) . |

*Primary Examiner*—Teresa Walberg
*Assistant Examiner*—Leonid M Fastovsky
(74) *Attorney, Agent, or Firm*—Griffin & Szipl, P.

(57) ABSTRACT

A heat radiator for emitting infrared radiation to the human body has a heat source which is energized to emit infrared radiation, whose penetration depth into the human body is to near warmth sensing points of the human body, and an insulator for covering the surface of the heat source to be directed toward the human body. The free surface of the insulator forms a surface for contacting with the human body and the thickness of the insulator is less than the penetration depth of the infrared radiation into the insulator.

41 Claims, 17 Drawing Sheets

U.S. PATENT DOCUMENTS

| | | | | |
|---|---|---|---|---|
| 5,879,378 | * | 3/1999 | Usai | 607/96 |
| 5,881,410 | * | 3/1999 | Yamada | 5/713 |
| 5,889,923 | * | 3/1999 | Lee et al. | 392/435 |
| 5,910,267 | * | 6/1999 | Sticker | 219/548 |
| 5,940,895 | * | 6/1999 | Wilson | 4/237 |
| 5,986,163 | * | 11/1999 | Augustine | 602/42 |
| 6,004,344 | * | 12/1999 | Fujii | 607/91 |
| 6,115,540 | * | 9/2000 | Klopotek | 392/432 |

* cited by examiner

HEAT RADIATOR

TECHNICAL FIELD

The present invention relates to a heat radiator which has a surface for contacting with the human body.

BACKGROUND ART

A heating apparatus such as heating floor, heating toilet seat, etc. has a surface for contacting with the human body. In conventional heating apparatuses having a surface for contacting with the human body, a heat source is energized to generate heat, the generated heat is transferred to an insulator covering the heat source, and the transferred heat is conducted to the surface of the insulator. Thus, the surface of the insulator, which forms a surface for contacting with the human body, is heated to an appropriate temperature. However, the infrared radiation from the heat source cannot be directly absorbed by the human body because it is completely absorbed by the insulator having large thickness.

A conventional heating apparatus, wherein the heat generated by a heat source passes to the surface of an insulator through heat transfer and heat conduction, thereby heating the human body in contact with the surface of the insulator, has a problem of not having quick heating capability because the speed of the heat passage through heat transfer and heat conduction is slow and it takes a long time before the surface of the insulator is heated to an appropriate temperature.

DISCLOSURE OF INVENTION

An object of the present invention is to provide a heating apparatus which has a surface for contacting with the human body and is excellent in quick heating capability.

According to the present invention, there is provided a heat radiator for emitting infrared radiation to the human body, comprising a heat source energized to emit infrared radiation, whose penetration depth into the human body is to near warmth sensing points of the human body, and an insulator covering the surface of the heat source directed toward the human body, wherein the free surface of the insulator forms a surface for contacting with the human body and the thickness of the insulator is less than the penetration depth of the infrared radiation into the insulator.

In the present heat radiator, the heat source is energized to generate heat and emit infrared radiation.

The heat generated by the heat source passes to the surface of the insulator through heat transfer and heat conduction. The thickness of the insulator is less than the penetration depth of the infrared radiation into the insulator. As a result, the thickness of the insulator is small. Thus, the heat generated by the heat source quickly passes to the free surface of the insulator, thereby quickly heating the free surface of the insulator which forms the surface for contacting with the human body to an appropriate temperature.

Part of the infrared radiation from the heat source is absorbed by the insulator and converted to heat. The infrared radiation is absorbed and converted to heat at every depth point of the insulator because the thickness of the insulator is less than the penetration depth of the infrared radiation into the insulator. The heat converted from the infrared radiation passes to the free surface of the insulator through heat conduction. The heat converted from the infrared radiation quickly passes to the free surface of the insulator because the infrared radiation is absorbed and converted to heat at every depth point of the insulator and the thickness of the insulator is small. Thus, the free surface of the insulator which forms the surface for contacting with the human body is quickly heated to an appropriate temperature.

Part of the infrared radiation from the heat source passes completely through the insulator to the outside to be absorbed by the human body in contact with the free surface of the insulator because the thickness of the insulator is less than the penetration depth of the infrared radiation into the insulator. This infrared radiation is completely absorbed by the human body and converted to heat by the time it reaches the vicinity of the warmth sensing points because the penetration depth of the infrared radiation into the human body is to near the warmth sensing points. Thus, the infrared radiation quickly heats the vicinity of the warmth sensing points to an appropriate temperature.

As is clear from the above description, the heat radiator in accordance with the present invention can quickly heat the free surface of the insulator, which forms the surface for contacting with the human body, to an appropriate temperature and also directly and quickly heat the vicinity of the warmth sensing points of the human body to an appropriate temperature. Thus, the heat radiator in accordance with the present invention has a high capability of quick heating. Thus, a heating apparatus into which the heat radiator in accordance with the present invention is incorporated has a high capability of quick heating.

The insulator is preferably made of a polyester resin such as polypropylene, polyethylene terephthalate, polybutylene terephthalate, polyethylene naphthalate, etc., or styrene resin such as acrylonitrile styrene, acrylonitrile butadiene styrene, etc. These resins have higher transmittance of infrared radiation than other resins. Thus, a major part of the infrared radiation from the heat source passes through an insulator made of any one of these resins to directly heat the human body. Thus, the quick heating capability of the heat radiator is further enhanced. Polyethylene terephthalate is highly effective to enhance the quick heating capability of the heat radiator because polyethylene terephthalate has high transmittance of long-wave infrared radiation, which is easily absorbed by the human body.

The insulator preferably adheres closely to the heat source. When the insulator adheres closely to the heat source, the heat transfer coefficient between the heat source and the insulator increases and the quick heating capability of the heat radiator increases. Adherence between the heat source and the insulator is enhanced by the use of a heat generating sheet as the heat source.

The heat source is preferably a porous heat generating sheet. When a porous heat generating sheet is bonded to the insulator, adhesive agent infiltrates into the pores of the heat generating sheet. Thus, the porous heat generating sheet adheres closely to the insulator. When a porous heat generating sheet is integrally molded with the insulator, resin material forming the insulator infiltrates into the pores of the heat generating sheet. Thus, the porous heat generating sheet adheres closely to the insulator. Thus, the quick heating capability of the heat radiator increases.

The porous heat generating sheet is preferably a mixed paper of carbon fibers and natural pulp fibers. The carbon fibers are efficient infrared radiators. The mixed paper of carbon fibers and natural pulp fibers is porous and can endure exposure to a high temperature fused resin. Thus, the heat generating sheet made of mixed paper of carbon fibers and natural pulp fibers is suitable for integral molding with an insulator made of resin. The carbon fibers are preferably surrounded by void spaces. The void spaces form heat insulating layers. Thus, the temperature of carbon fibers surrounded by void spaces quickly rises after the mixed paper is energized. Thus, carbon fibers quickly emit infrared radiation after the mixed paper is energized. Thus, the quick heating capability of the heat radiator increases.

The void ratio of the mixed paper is preferably equal to or greater than 60 volume %. When the void ratio of the mixed paper is equal to or greater than 60 volume % air layers or heat insulating layers are reliably formed around the carbon fibers. Thus, the temperature rising speed of the carbon fibers increases and the time from the start of the energizing of the mixed paper to the start of the emission of the infrared radiation decreases. Thus, the quick heating capability of the heat radiator increases.

The heat radiator may be provided with a infrared reflector facing the surface of the heat source directed away from the human body. The infrared rays radiated away from the human body are reflected toward the human body, thereby contributing to temperature increase of the human body. Thus, the quick heating capability of the heat radiator increases.

According to the present invention, there is provided a heating apparatus having a heat radiator as described above, the heating apparatus comprising a front surface resin layer opposing the human body and a rear surface resin layer, wherein the front surface resin layer forms the insulator of the heat radiator covering the surface of the heat source directed toward the human body, and the front surface resin layer and the rear surface resin layer cooperate to sandwich the heat source of the heat radiator.

The thickness of the front surface resin layer is less than the penetration depth of the infrared radiation into the front surface resin layer. Thus, the front surface resin layer is thin and does not have sufficient strength against external forces. However, the front surface resin layer is reinforced by the rear surface resin layer when the front surface resin layer and the rear surface resin layer cooperate to sandwich the heat source. Thus, a heating apparatus which has a quick heating capability and sufficient strength against external forces can be obtained.

The front surface resin layer and the rear surface resin layer must be united into an integral body so as to reinforce the front surface resin layer by the rear surface resin layer. The following processes are preferable to unite them into an integral body.

① A process comprising the steps of inserting projections extending from the front surface resin layer and penetrating through the heat source into penetration holes formed in the rear surface resin layer, and heat fusing the end portions of the projections to form swellings.

② A process comprising a step of inserting projections extending from the front surface resin layer to penetrate through the heat source and being provided with swellings at their ends into penetration holes formed in the rear surface resin layer.

In the process ① or ②, the front surface resin layer and the rear surface resin layer are mechanically united. Thus, they can be reliably united into an integral body even if they are hard to bond together.

③ A process comprising the steps of abutting the front surface resin layer against the rear surface resin layer and energizing an electric wire embedded beforehand in the abutting surface of the rear surface resin layer or the front surface resin layer to fuse and bond the abutting surfaces.

In the process ③, since the bonded surface can be easily re-fused by energizing the electric wire, the front surface resin layer can be removed from the rear surface resin layer to enable removal of the heat source from the heating apparatus. Thus, reuse of the heat source is expedited.

④ A process comprising the steps of placing the heat source on the premolded front surface resin layer or the premolded rear surface resin layer, placing the premolded front surface resin layer carrying the heat source or the premolded rear surface resin layer carrying the heat source in a mold for low pressure molding, pouring resin material of the rear surface resin layer or the front surface resin layer into the mold, and closing the mold to carry out low pressure molding.

In the process ④, the unity between the front surface resin layer and the rear surface resin layer increases and the strength of the heating apparatus against external forces increases. Quick heating capability of the heating apparatus increases because adherence of the heat source to the front resin layer increases. Low pressure molding protects the heat source from damage during the molding operation.

In the process ④, the premolded front surface resin layer or the premolded rear surface resin layer may be provided with projections for immobilizing the heat source. Thus, the heat source is kept from sliding during the molding operation. When a heat generating sheet is used as the heat source, the heat generating sheet is kept from sliding and crumpling.

In the process ④, the premolded rear surface resin layer may be provided with irregularities or grooves in the surface receiving the heat source. Thus, the front surface resin layer intrudes into the irregularities or grooves to be firmly united with the rear surface resin layer as an integral body. Thus, the strength of the heating apparatus against external forces increases.

⑤ A process comprising the steps of molding the front surface resin layer or the rear surface resin layer, holding the molded front surface resin layer or the molded rear surface resin layer in the mold, placing the heat source on the front surface resin layer or the rear surface resin layer, pouring resin material of the rear surface resin layer or the front surface resin layer into the mold, and closing the mold to carry out low pressure molding.

In the process ⑤, the same effects as in the process ④ can be obtained. In the process ⑤, the front surface resin layer, the heat source and the rear surface resin layer can be united into an integral body by a continuous series of processes. Thus, the trouble of transferring partially fabricated items such as the premolded front surface resin layer, the premolded rear surface resin layer, etc., and placing them in the mold can be avoided.

⑥ A process comprising the steps of vacuum attracting a resin film to a mold for low pressure molding, placing the heat source on the resin film, pouring resin material of the rear surface resin layer into the mold, and closing the mold to carry out low pressure molding.

In the process ⑥, the same effects as in the process ④ can be obtained. In the process ⑥, the distribution of the thickness of the front surface resin layer can be made even and the the thickness of the front surface resin layer can be made small. When the distribution of the thickness of the front surface resin layer is even, the temperature distribution of the free surface of the front surface resin layer which forms the surface for contacting with the human body is even. Thus, the comfort of the eating apparatus is enhanced. When the thickness of the front surface resin layer is small, the quantity of infrared radiation passing through the front surface resin layer increases and the quick heating capability of the heating apparatus increases.

⑦ A process comprising the steps of placing the heat source on a first mold for low pressure molding, pouring resin material of the front surface resin layer or the rear surface resin layer into the mold, closing the mold to carry out low pressure molding to unite the front surface resin layer or the rear surface resin layer and the heat source into an integral body, placing the front surface resin layer united with the heat source or the rear surface resin layer united with the heat source in a second mold for low pressure molding, pouring resin material of the rear surface resin layer or the front surface resin layer into the mold, and closing the mold to carry out low pressure molding.

In the process ⑦, unity between the front surface resin layer and the rear surface resin layer increases and the strength of the heating apparatus against external forces increases. Quick heating capability of the heating apparatus increases because adherence of the heat source to the front surface resin layer increases.

In the process ⑦, the first mold for low pressure molding may be provided with projections for immobilizing the heat source. Thus, the heat source is kept from sliding during the molding operation. When a heat generating sheet is used as the heat source, the heat generating sheet is kept from sliding and crumpling.

In the processes ① to ⑦, the heat source may be given the same color as the front surface resin layer. In this case, the heat source cannot be seen through and users of the heating apparatus do not feel uneasy even if the front surface resin layer is light colored.

In the processes ① to ①, the front surface resin layer and/or the rear surface resin layer may be foamed resin layers. Thus, the heating apparatus becomes flexible and the comfort of the heating apparatus is enhanced.

In the processes ① to ⑦, the heat source may be wrapped with a resin film beforehand. In this case, the heat source is protected from damage when the front surface resin layer, the heat source and the rear surface resin layer are united into an integral body and the manufacturing efficiency of the heating apparatus increases because handling of the heat source becomes easy.

When the heat source is wrapped with a resin film beforehand, the portion of the resin film opposing the rear surface resin layer may be an infrared radiation reflection film. In this case, the infrared radiation in the direction away from the human body is reflected toward the human body by the infrared radiation reflection film, thereby contributing to the temperature increase of the human body. Thus, the quick heating capability of the heat radiator increases.

In any one of the processes ① to ③, a cushioning layer may be sandwiched between the rear surface resin layer and the heat source. When the front surface resin layer, the heat source and the rear surface resin layer are united into an integral body by any one of the processes ① to ③, there is a possibility of their not being sufficiently united into an integral body because of size mismatch between the front surface resin layer and the rear surface resin layer caused by manufacturing error. However, if a cushioning layer is sandwiched between the rear surface resin layer and the heat source, any size mismatch between the front surface resin layer and the rear surface resin layer is absorbed by the cushioning layer. Thus, sufficient unity can be obtained.

When a cushioning layer is sandwiched between the rear surface resin layer and the heat source, the cushioning layer may be integrally molded with the rear surface resin layer. Thus, the trouble of inserting the cushioning layer between the front surface resin layer and the rear surface resin layer can be avoided when the front surface resin layer, the heat source and the rear surface resin layer are united into an integral body. Thus, the manufacturing efficiency of the heating apparatus increases.

When a cushioning layer is sandwiched between the rear surface resin layer and the heat source, the cushioning layer may be a heat insulator. In this case, the heat generated by the heat source is not absorbed by the cushioning layer, the heating efficiency of the heat source increases and the quick heating capability of the heating apparatus increases.

In any one of the processes ① to ⑦ the rear surface resin layer may be honeycombed. In this case, the weight of the heating apparatus is reduced.

In any one of the processes ① to ①, the rear surface resin layer may be provided with a hollow wherein a heat sensor is received. In this case, the heat source can be precisely controlled and the heating apparatus can be precisely controlled.

If the temperature distribution of the heat source is uneven, the front surface resin layer facing the higher temperature portion of the heat source may be made thick and the front surface resin layer facing the lower temperature portion of the heat source may be made thin. In this case, temperature distribution of the free surface of the front surface resin layer which forms the surface for contacting with the human body becomes even and the comfort of the heating apparatus is enhanced.

The heating apparatus in accordance with the present invention can be applied as various kinds of heating apparatuses such as room heating apparatuses, toilet heating apparatuses, etc. Examples of room heating apparatuses are floor heating panels, wall heating panels, heating carpets, heating panels, etc. Examples of toilet heating apparatuses are heating toilet mats, heating panels, heating toilet seat covers, heating toilet seats, etc. The heating apparatus in accordance with the present invention wherein the heat source is flexible and the front surface resin layer and the rear surface resin layer are made of flexible material can be applied to a heating robe, winter clothes, a chair seat, a chair backrest, a chair armrest, etc.

The room heating apparatus in accordance with the present invention may further comprise a human body detecting apparatus which can detect the presence of a person in a room and a heat source controller which energizes the heat source only when the human body detecting apparatus detects the presence of a person. Thus, the electric power consumption of the room heating apparatus is reduced because the room heating apparatus operates only when a person is present in the room.

The toilet heating apparatus in accordance with the present invention may further comprise a heat source controller which energizes the heat source in accordance with a control signal from outside the toilet. Thus, the toilet heating apparatus can be started just before a person enters the toilet and stopped just after the person leaves the toilet. Thus, the toilet can be comfortably used and the electric power consumption of the toilet heating apparatus can be reduced.

The toilet heating apparatus in accordance with the present invention may further comprise a heat source controller which energizes the heat source only when an electric lamp in the toilet is switched on. In an ordinary home, the toilet light is switched on only when the toilet is used. Thus, the above described heat source controller enables comfortable use of the toilet as well as reduction of electric power consumption.

The toilet heating apparatus in accordance with the present invention may further comprise the human body detecting apparatus which can detect the presence of a person in a toilet and a heat source controller which energizes the heat source only when the human body detecting apparatus detects the presence of a person. Thus, the electric power consumption of the toilet heating apparatus is reduced because the toilet heating apparatus operates only when a person is present in the toilet.

In the toilet heating apparatus further comprising the human body detecting apparatus which can detect the presence of a person in a toilet and a heat source controller which energizes the heat source only when the human body detecting apparatus detects the presence of a person, the heat source controller can be adapted to energize the heat source a predetermined time after the human body detecting apparatus detects a person. The human body detecting apparatus detects a person just after the person enters the toilet. Around 10 to 20 seconds pass between the time a person enters the toilet and the time the person sits on the toilet seat. Thus, even if the heat source controller energizes the heat source a predetermined time after the human body detecting apparatus detects the presence of a person, some time is still available between the time the heat source is energized and the time the person sits on the toilet seat. The surface of the toilet heating apparatus for contacting with the human body can be reliably heated to an appropriate temperature during the available time because the toilet heating apparatus in accordance with the present invention is excellent in quick heating capability. Thus, the electric power consumption of the toilet heating apparatus is reduced without impairing the comfort of the toilet heating apparatus owing to the delayed turnon of the toilet heating apparatus.

In the toilet heating apparatus further comprising the human body detecting apparatus which can detect the presence of a person in the toilet and a heat source controller which energizes the heat source only when the human body detecting apparatus detects a person, the heat source controller can be adapted to energize the heat source at time T-t after the human body detecting apparatus detects a person, where T is the time between detection of the person by the human body detecting apparatus and seating of the person on the toilet seat, and t is the time from energizing of the heat source to the completion of the heating of the front surface resin layer to a predetermined temperature. By this, the electric power consumption of the toilet heating apparatus is reduced without impairing the comfort of the toilet heating apparatus owing to the above-mentioned delayed turnon of the toilet heating apparatus.

In the toilet heating apparatus further comprising the human body detecting apparatus which can detect the presence of a person in the toilet and a heat source controller which energizes the heat source only when the human body detecting apparatus detects a person, the human body detecting apparatus can be adapted to detect the distance between the human body detecting apparatus and the person, and the heat source controller can be adapted to energize the heat source when the distance between the human body detecting apparatus and the person becomes a predetermined value. In this case, if the human body detecting apparatus is located near the toilet seat, the toilet heating apparatus can be started when the person reaches a point a predetermined distance from the toilet seat. In this case, the electric power consumption of the toilet heating apparatus is reduced owing to the delayed turnon of the toilet heating apparatus.

In the toilet heating apparatus in accordance with the present invention, the temperature coefficient of resistance of the heat source may be positive. In this case, the temperature of the energized heat source asymptotically approaches a constant level because the resistance of the heat source increases and the electric current flowing through the heat source decreases as the temperature of the heat source increases. Thus, the toilet heating apparatus is prevented from overheating.

In the toilet heating apparatus in accordance with the present invention, the heat source controller can be adapted to variably control the electric power supply to the heat source. In this case, the toilet heating apparatus is prevented from overheating and also reliably heated to an appropriate temperature even if the environmental conditions such as room temperature, etc. have changed.

In the toilet heating apparatus in accordance with the present invention, the heat source controller can be adapted to vary the electric power supply to the heat source stepwise. In this case, the toilet heating apparatus is prevented from overheating.

In the toilet heating apparatus in accordance with the present invention, the heat source controller can be adapted to determine the electric power supply to the heat source by feedback control. By this, the toilet heating apparatus is quickly heated to an appropriate temperature and prevented from overheating.

In the toilet heating apparatus in accordance with the present invention, the heat source controller can be adapted to determine the electric power supply to the heat source by learning control. By this, deviation from standard performance of the toilet heating apparatus at shipment can be corrected based on the performance at the first operation, so that the toilet heating apparatus can exhibit the expected performance from the second operation.

The toilet heating apparatus in accordance with the present invention may further comprise a seating detection apparatus which detects the seating of a person on the toilet seat, and the heat source controller may be adapted to decrease the electric power supply to the heat source when the seating detection apparatus detects the seating of a person on the toilet seat. This feature can be used in an arrangement in which, after a person sits on the toilet seat, the person's feet contact the toilet heating mat placed near the toilet seat, buttocks contact the heating toilet seat and the back contacts the heating toilet seat cover to keep them warm. By this, the comfort of the toilet heating apparatus is not impaired even if the electric power supply to the toilet heating apparatus is reduced after the person sits on the toilet seat. Thus, the electric power consumption of the toilet heating apparatus is reduced by reducing the power supply to the toilet heating apparatus.

BRIEF DESCRIPTION OF THE DRAWINGS

In the drawings:

FIG. 21 is a sectional view of a heating apparatus in accordance with a preferred embodiment of the present invention which is embodied as a heating toilet seat.

FIG. 22 is a sectional view of the heating apparatus of FIG. 21 and molds showing the fabrication process of the heating apparatus.

FIG. 26 is a sectional view of a heating apparatus in accordance with a preferred embodiment of the present invention which is embodied as a heating toilet seat.

FIG. 27 is a sectional view of a heating apparatus in accordance with a preferred embodiment of the present invention which is embodied as a heating toilet seat.

THE BEST MODE FOR CARRYING OUT THE INVENTION

A heat radiator in accordance with a preferred embodiment of the present invention will be described.

Figure 1:
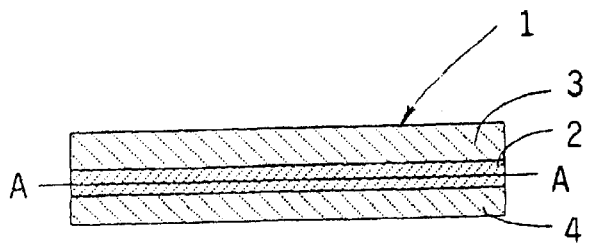
FIG. 1(a) is a sectional view of a heat radiator in accordance with a preferred embodiment of the present invention.
FIG. 1(b) is the sectional view of FIG. 1(a) along line A—A.
Figure 1:
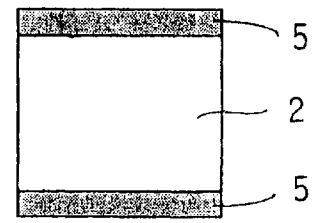

As shown in FIGS. 1(a) and 1(b), a heat radiator 1 has a heat source or a heat generating sheet 2, an insulator 3 for covering the surface of the heat generating sheet 2 to be directed toward the human body, an insulator 4 for covering the surface of the heat generating sheet 2 to be directed away from the human body and a pair of electrodes 5. The free surface of the insulator 3 forms a surface for contacting with the human body.

The heat generating sheet 2 is energized to generate heat and emit infrared radiation whose penetration depth into the human body is to near warmth sensing points of the human body.

By warmth sensing points of the human body is meant a portion of the skin of the human body where thermal receptors for sensing warmth exist. The warmth sensing points of the human body are located 200 to 300 $\mu$m below the surface of the skin.

The infrared radiation entering the body is absorbed as it passes through the body. Any unabsorbed infrared radiation passes out of the body. The transmittance $\tau$ of the infrared radiation is expressed by the formula $\tau=I_1/I_0$, wherein $I_0$ is the incident energy and $I_1$ is the transmission energy. The transmittance $\tau$ varies with the characteristics and the thickness of the body. The relation between the transmittance $\tau$ the infrared absorption coefficient $\mu$ of the body and the thickness x of the body is expressed by the formula $\tau=\exp(-\mu x)$. The infrared absorption coefficient $\mu$ varies with the characteristics of the body and the wavelength of the infrared. The penetration depth indexes whether the infrared radiation can pass through the body or not. The penetration depth is the travel distance of the infrared radiation into the body before it damps to ¹⁄₁₀. In other words, the penetration depth is the thickness of the body resulting in a transmittance $\tau$ of 10% . The penetration depth varies with the characteristics of the body and the wavelength of the infrared radiation. The penetration depth into the human body of infrared radiation with a wavelength of 2.5 to 50 $\mu$m is 200 to 300 $\mu$m.

The thickness of the insulator 3 is made less than the penetration depth of the infrared radiation into the insulator 3. The penetration depth of infrared radiation with a wavelength of 3 to 12 $\mu$m into an insulator 3 made of polypropylene is about 1.5 mm. The penetration depth of infrared radiation with a wavelength of 3 to 12 $\mu$m into an insulator 3 made of acrylonitrile butadiene styrene is about 390 $\mu$m.

In the heat radiator 1, a predetermined voltage is applied between the pair of electrodes 5 to energize the heat generating sheet 2. Thus, the heat generating sheet 2 is heated and emits infrared radiation.

The heat generated by the heat generating sheet 2 passes to the free surface of the insulator 3 through heat transfer and heat conduction. The thickness of the insulator 3 is less than the penetration depth of the infrared radiation into the insulator 3. As a result, the thickness of the insulator 3 is small. Thus, the heat generated by the heat generating sheet 2 quickly passes to the free surface of the insulator 3, thereby quickly heating the free surface of the insulator 3, which forms the surface for contacting with the human body, to an appropriate temperature.

Part of infrared radiation from the surface of the heat generating sheet 2 directed toward the human body is absorbed by the insulator 3 and converted to heat. The infrared radiation is absorbed and converted to heat at every depth point of the insulator 3 because the thickness of the insulator 3 is less than the penetration depth of the infrared radiation into the insulator 3. The heat converted from the infrared radiation passes to the free surface of the insulator 3 through heat conduction. The heat converted from the infrared radiation quickly passes to the free surface of the insulator 3 because the infrared radiation is absorbed and converted to heat at every depth point of the insulator 3 and the thickness of the insulator 3 is small. Thus, the free surface of the insulator 3, which forms the surface for contacting with the human body, is quickly heated to an appropriate temperature.

Part of infrared radiation from the heat generating sheet 2 passes completely through the insulator 3 to the outside to be absorbed by the human body in contact with the free surface of the insulator 3 because the thickness of the insulator 3 is less than the penetration depth of the infrared radiation into the insulator 3. This infrared radiation is completely absorbed by the human body and converted to heat by the time it reaches the vicinity of the warmth sensing points because the penetration depth of the infrared radiation into the human body is to near the warmth sensing points. Thus, the infrared radiation quickly heats the vicinity of the warmth sensing points to an appropriate temperature.

As is clear from the above description, the heat radiator 1 in accordance with this preferred embodiment of the present invention can quickly heat the free surface of the insulator 3, which forms the surface for contacting with the human body, to an appropriate temperature and also directly and quickly heat the vicinity of the warmth sensing points of the human body to an appropriate temperature. Thus, the heat radiator 1 in accordance with this preferred embodiment of the present invention has a high capability of quick heating. Thus, a heating apparatus into which the heat radiator 1 in accordance with this preferred embodiment of the present invention is incorporated has a high capability of quick heating.

The insulator 3 is preferably made of a polyester resin such as polypropylene, polyethylene terephthalate, polybutylene terephthalate, polyethylene naphthalate, etc., or styrene resin such as acrylonitrile styrene, acrylonitrile butadiene styrene, etc. These resins have higher transmittance of infrared radiation than other resins. Thus, the major part of the infrared radiation from the heat generating sheet 2 passes through the insulator 3 made of one of these resins to directly heat the human body. Thus, quick heating capability of the heat radiator 1 is further enhanced. Polyethylene terephthalate is highly effective to enhance the quick heating capability of the heat radiator 1 because polyethylene terephthalate has high transmittance of long-wave infrared radiation which is easily absorbed by the human body.

The heat generating sheet 2 preferably adheres closely to the insulator 3. When the heat generating sheet 2 adheres closely to the insulator 3, the heat transfer coefficient between the heat generating sheet 2 and the insulator 3 increases and the quick heating capability of the heat radiator 1 increases. Generally speaking, a heat generating sheet can adhere closely to the insulator covering it.

The heat generating sheet 2 is preferably porous. When the porous heat generating sheet 2 is bonded to the insulator 3, adhesive agent infiltrates into the pores of the heat generating sheet 2. Thus, the porous heat generating sheet 2 adheres closely to the insulator 3. When the porous heat generating sheet 2 is integrally molded with the insulator 3, resin material forming the insulator 3 infiltrates into the pores of the heat generating sheet 2. Thus, the porous heat generating sheet 2 adheres closely to the insulator 3. Thus, the quick heating capability of the heat radiator 1 increases.

Figure 2:
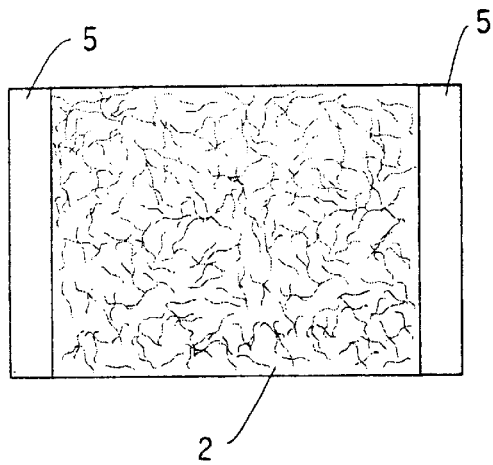
FIG. 2 is a plan view of the heat generating sheet of a heat radiator in accordance with a preferred embodiment of the present invention.
Figure 3:
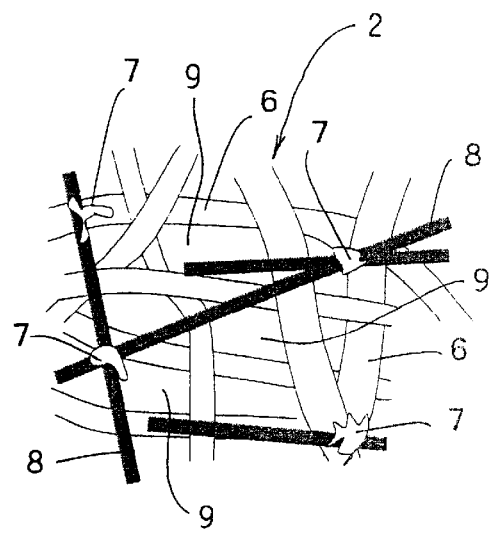
FIG. 3 is a partially enlarged view of FIG. 2.

As shown in FIGS. 2 and 3, the porous heat generating sheet 2 is preferably a mixed paper of carbon fibers and natural pulp fibers. The porous heat generating sheet 2 shown in FIGS. 2 and 3 is a mixed paper of carbon fibers 8 and natural pulp fibers 6. The mixed paper is made by a process comprising the steps of mixing natural pulp fibers 6 such as hemp pulp fibers, etc., binder 7 made of PVA resin, carbon fibers 8 and water to make a pulp solution, pouring the pulp solution on a net to make a wet sheet, mechanically drying the wet sheet with a roller to make a dry sheet, and heating the dry sheet to fuse the binder 7, thereby bonding point contact portions between the carbon fibers 8 and point contact portions between the carbon fibers 8 and natural pulp fibers 6. The heat generating sheet 2 made of a mixed paper of carbon fibers 8 and natural pulp fibers 6 has stable resistance because the point contact portions between the carbon fibers 8 are stably maintained by the binder 7. When voltage is applied between the pair of electrodes 5 connected to the opposite ends of the heat generating sheet 2 made of a mixed paper, electric current flows through the carbon fibers 8 to heat the carbon fibers 8 by Joule heat. The carbon fibers 8 therefore emit infrared radiation. The mixed paper shown in FIGS. 2 and 3 contains 25 weight % of 1 to 5 mm long carbon fibers, weighs 20.5 g/m$^2$, and is about 200 $\mu$m thick. As shown in FIG. 3, void spaces 9 are formed around the carbon fibers 8.

The carbon fibers 8 are efficient infrared radiators. The mixed paper of the carbon fibers 8 and the natural pulp fibers 6 is porous and can endure exposure to a high temperature fused resin. Thus, the heat generating sheet 2 made of a mixed paper of the carbon fibers 8 and the natural pulp fibers 6 is suitable for integral molding with the insulator 3 made of resin. The carbon fibers 8 are preferably surrounded by void spaces 9. The void spaces 9 form heat insulating layers. Thus, the temperature of the carbon fibers 8 surrounded by the void spaces 9 quickly rises after the mixed paper is energized. Thus, the carbon fibers 8 quickly emit infrared radiation after the mixed paper is energized. Thus, the quick heating capability of the heat radiator 1 increases.

The void ratio of the mixed paper is preferably equal to or greater than 60 volume %. When the void ratio of the mixed paper is equal to or greater than 60 volume %, air layers or heat insulating layers are reliably formed around the carbon fibers 8. Thus, the temperature increase rate of the carbon fibers 8 increases and the time from the start of the energizing of the mixed paper to the start of the emission of the infrared radiation decreases. Thus, the quick heating capability of the heat radiator 1 increases.

Figure 4:
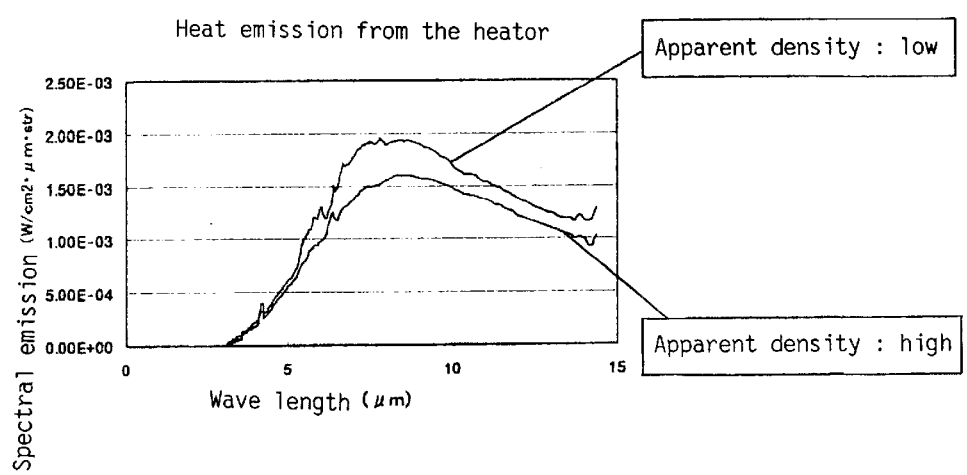
FIG. 4 is a diagram showing the heat emission from a heat generating sheet.

It is preferable for a 200 μm thick mixed paper to have a weight equal to or less than 21 g/m² so as to have an apparent density equal to or less than 0.105 g/cm³. When the mixed paper has an apparent density greater than 0.15 g/cm³, the void ratio of the mixed paper decreases, the temperature increase rate of the carbon fibers 8 decreases, and the quick heating capability of the heat radiator 1 decreases. FIG. 4 shows a comparison of spectral emission corresponding to rated electric power consumption between a mixed paper with an apparent density of 0.11 g/cm³ and a mixed paper with an apparent density of 0.5 g/Cm³. As is clear from FIG. 4, the spectral emission of the mixed paper with smaller apparent density is larger than that of the mixed paper with larger apparent density.

Figure 5:
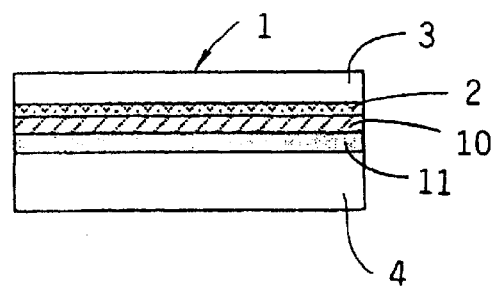
FIG. 5 is a sectional view of a heat radiator in accordance with another preferred embodiment of the present invention.

As shown in FIG. 5, the heat radiator 1 may be provided with an infrared reflector 10 facing the surface of the heat generating sheet 2 directed away from the human body and a heat insulator 11 facing the infrared reflector 10. The infrared radiation from the surface of the heat generating sheet 2 directed away from the human body is reflected toward the human body by the infrared reflector 10, thereby contributing to temperature increase of the human body. Thus, the quick heating capability of the heat radiator 1 increases. Transfer of heat generated by the heat generating sheet 2 to the insulator 4 is blocked by the heat insulator 11. Thus, the temperature increase rate of the insulator 3 increases and the quick heating capability of the heat radiator 1 increases.

A heating apparatus having the heat radiator 1 will be described.

Figure 6:
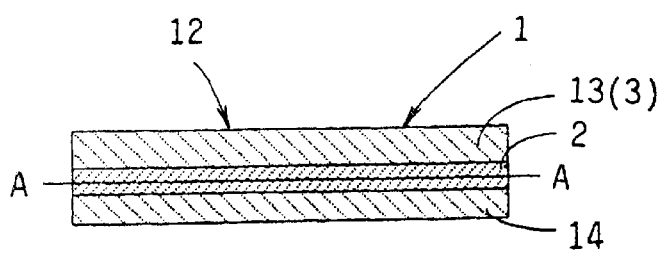
FIG. 6(a) is a sectional view of a heating apparatus in accordance with a preferred embodiment of the present invention.
FIG. 6(b) is the sectional view of FIG. 6(a) along line A—A.
Figure 6:
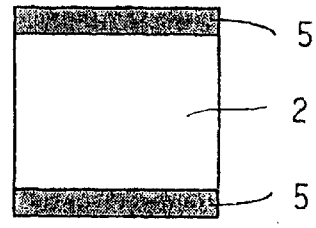

As shown in FIGS. 6(*a*) and 6(*b*), a heating apparatus 12 comprises a front surface resin layer 13 to be directed toward the human body and a rear surface resin layer 14. The front surface resin layer 13 forms the insulator 3 of the heat radiator 1 covering the surface of the heat generating sheet 2 directed toward the human body. The front surface resin layer 13 and the rear surface resin layer 14 cooperate to sandwich the heat generating sheet 2 of the heat radiator 1. A pair of electrodes 5 are connected to the opposite ends of the heat generating sheet 2.

The thickness of the front surface resin layer 13 is less than the penetration depth of the infrared radiation into the front surface resin layer 13. Thus, the front surface resin layer 13 is thin and does not have sufficient strength against external forces. However, the front surface resin layer 13 can be reinforced by the rear surface resin layer 14 if the front surface resin layer 13 and the rear surface resin layer 14 cooperate to sandwich the heat generating sheet 2. Thus, a heating apparatus 12 which has a quick heating capability and sufficient strength against external forces can be obtained.

The front surface resin layer 13 and the rear surface resin layer 14 must be united into an integral body so as to reinforce the front surface resin layer 13 by the rear surface resin layer 14. The following processes are preferable to unite them into an integral body.

(1) Process 1

Figure 7:
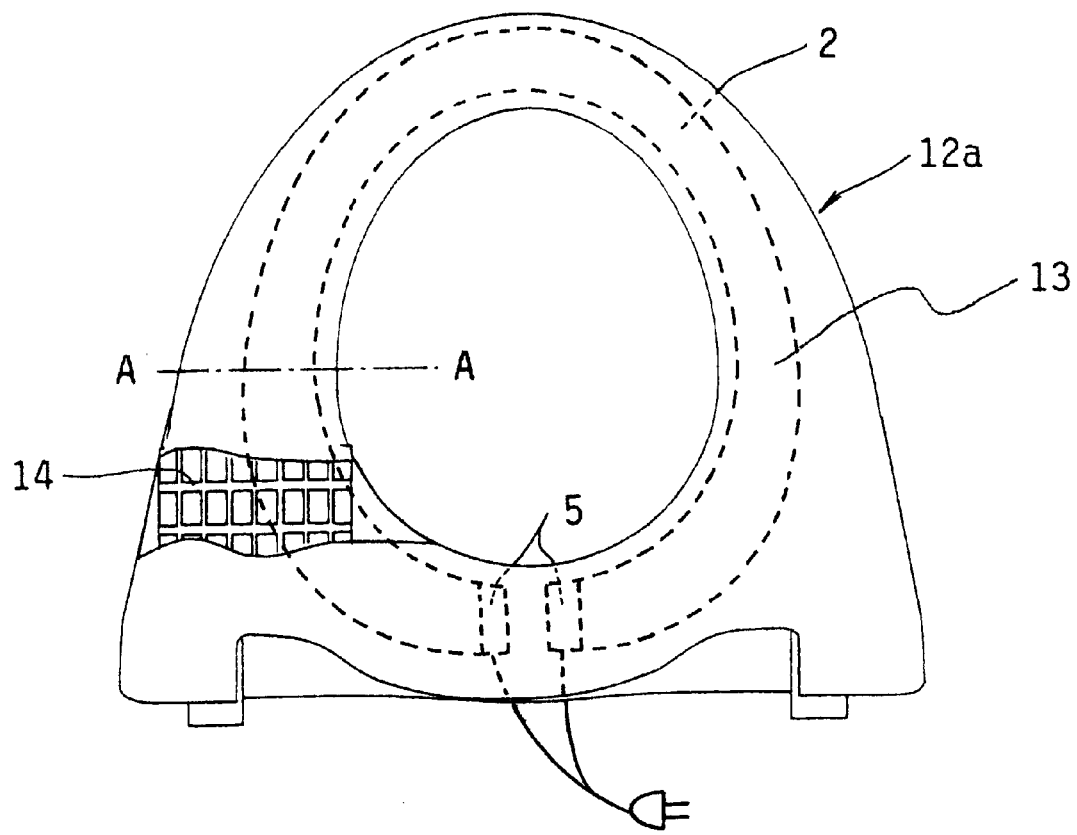
FIG. 7 is the top view of a heating apparatus in accordance with a preferred embodiment of the present invention which is embodied as a heating toilet seat.
Figure 8:
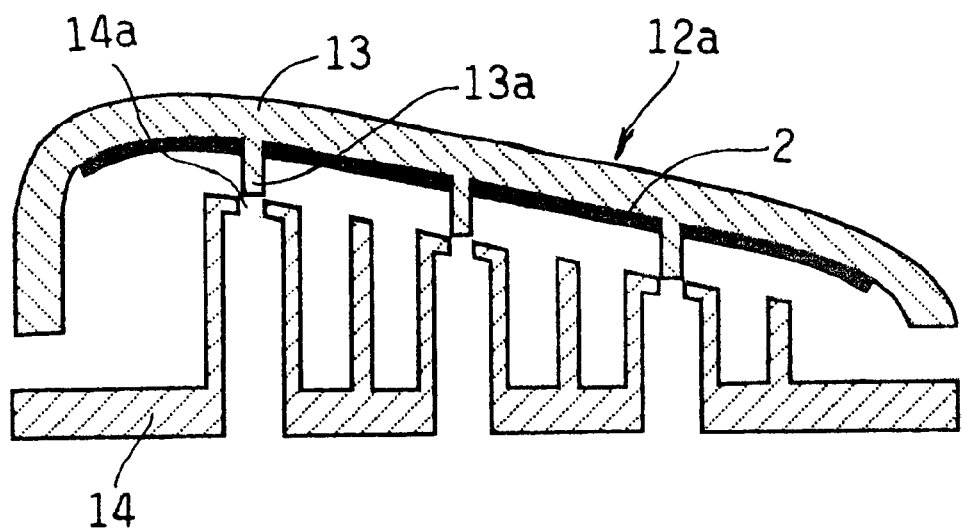
FIGS. 8(a) and 8(b) are the sectional views of FIG. 7 along line A—A.
Figure 8:
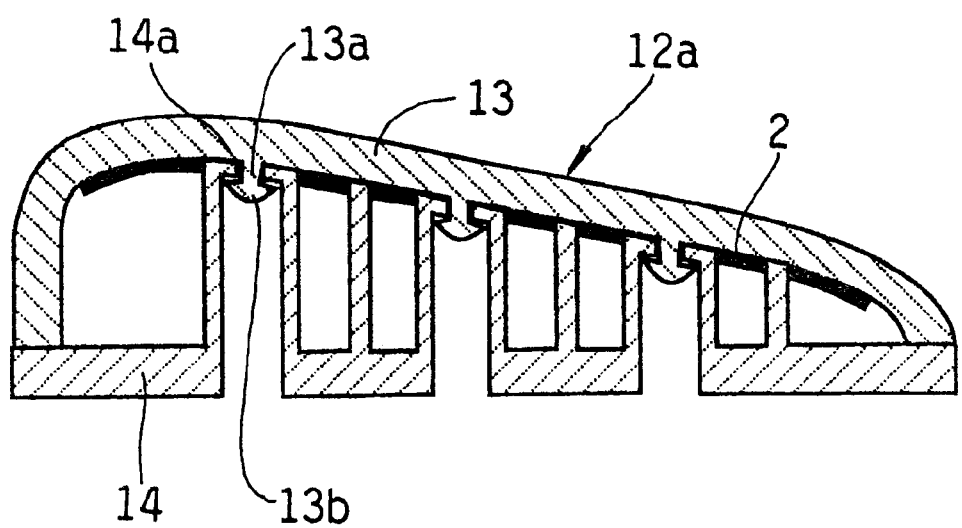

As shown in FIGS. 7 and 8(*b*), a heating apparatus 12*a* which is embodied as a heating toilet seat comprises a front surface resin layer 13, a rear surface resin layer 14 and a horseshoe-shaped heat generating sheet 2. A pair of electrodes 5 are connected to the opposite ends of the heat generating sheet 2. Electric wires extend from the electrodes 5. The rear surface resin layer 14 is honeycombed. The front surface resin layer 13 and the rear surface resin layer 14 cooperate to sandwich the heat generating sheet 2. The free surface of the front surface resin layer 13 forms a surface for contacting with the human body. Projections 13*a* extending from the front surface resin layer 13 and penetrating the heat generating sheet 2 are inserted into penetration holes 14*a* formed in the rear surface resin layer 14. The end portions of the projections 13*a* are then formed with swellings 13*b* larger than the diameters of the penetration holes 14*a*. The front surface resin layer 13 and the rear surface resin layer 14 are mechanically united into an integral body by the projections 13*a*.

The heating apparatus 12*a* is fabricated by the following process. As shown in FIG. 8(*a*), the projections 13*a* extending from the front surface resin layer 13 are inserted into penetration holes formed in the heat generating sheet 2. The heat generating sheet 2 is bonded to the front surface resin layer 13. As shown in FIG. 8(*b*), the projections 13*a* are inserted into penetration holes 14*a* formed in the rear surface resin layer 14. The end portions of the projections 13*a* are heat fused to form swellings 13*b*.

In the process 1, the front surface resin layer 13 and the rear surface resin layer 14 are mechanically united. Thus, they can be reliably united into an integral body even if they are hard to bond together.

(2) Process 2

Figure 9:
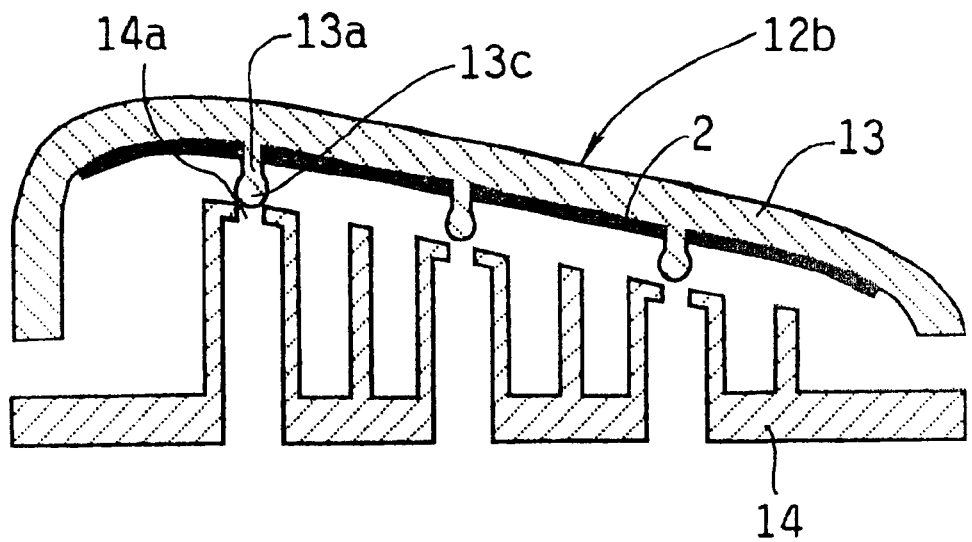
FIGS. 9(a) and 9(b) are sectional views of a heating apparatus in accordance with a preferred embodiment of the present invention which is embodied as a heating toilet seat.
Figure 9:
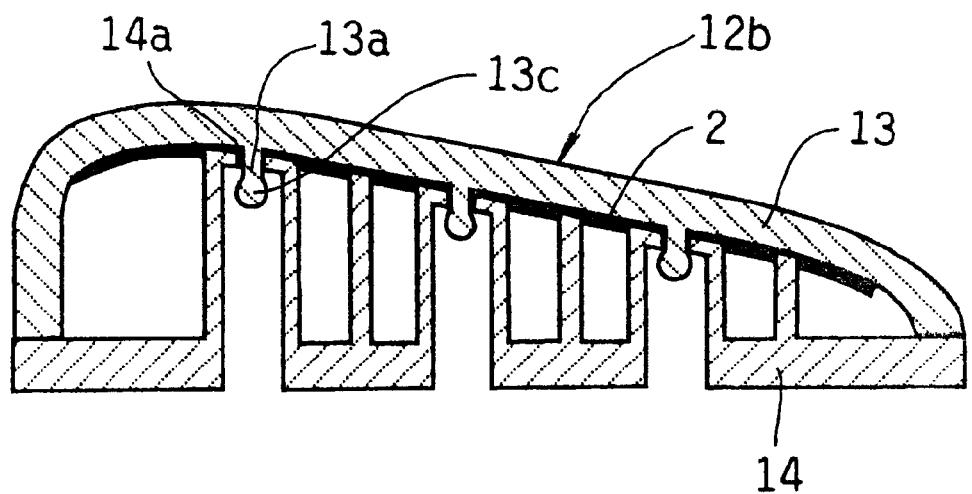

As shown in FIG. 9(*b*), a heating apparatus 12*b* which is embodied as a heating toilet seat has the same structure as that of the heating apparatus 12*a*. However, the ends of the projections 13*a* extending from the front surface resin layer 13 are provided beforehand with premolded swellings 13*c*.

The heating apparatus 12*b* is fabricated by the following process. As shown in FIG. 9(*a*), the projections 13*a* extending from the front surface resin layer 13 are inserted into penetration holes formed in the heat generating sheet 2. The heat generating sheet 2 is bonded to the front surface resin layer 13. As shown in FIG. 9(*b*), the projections 13*a* provided at their ends with the premolded swellings 13*c* are inserted into penetration holes 14*a* formed in the rear surface resin layer 14. The swellings 13*c* resiliently deform to penetrate the holes 14*a*.

In the process 2, the front surface resin layer 13 and the rear surface resin layer 14 are mechanically united. Thus, they can be reliably united into an integral body even if they are hard to bond together.

(3) Process 3

Figure 10:
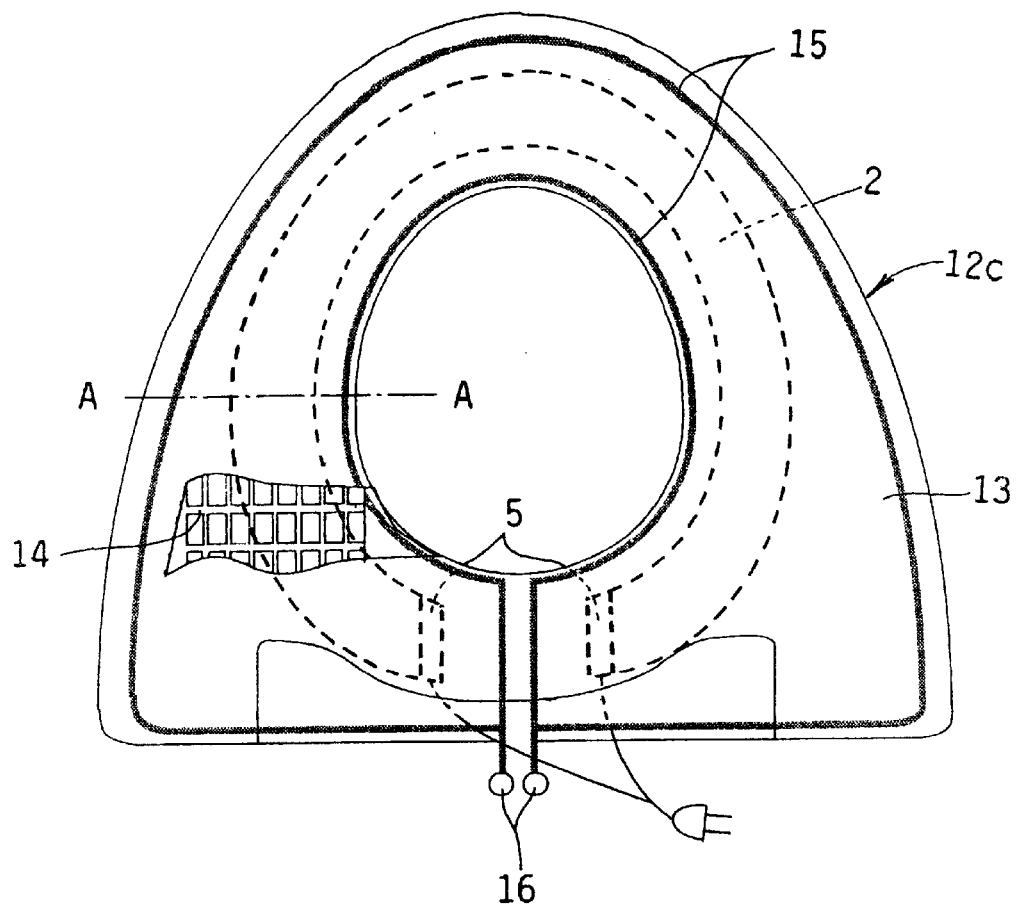
FIG. 10 is the top view of a heating apparatus in accordance with a preferred embodiment of the present invention which is embodied as a heating toilet seat.
Figure 11:
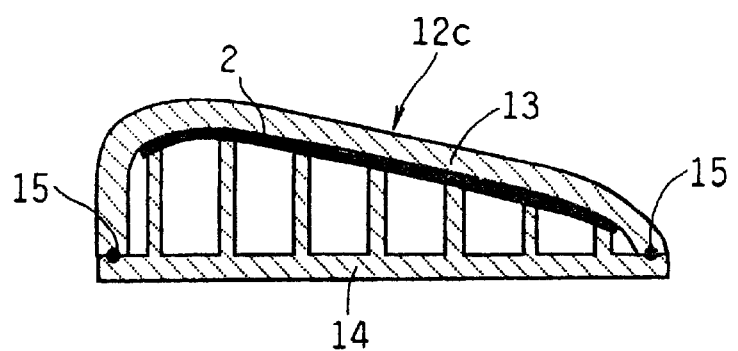
FIG. 11 is the sectional view of FIG. 10 along line A—A.

As shown in FIGS. 10 and 11, a heating apparatus 12*c* which is embodied as a heating toilet seat comprises a front surface resin layer 13, a rear surface resin layer 14 and a horseshoe-shaped heat generating sheet 2. A pair of electrodes 5 are connected to the opposite ends of the heat generating sheet 2. Electric wires extend from the electrodes 5. The rear surface resin layer 14 is honeycombed. The front surface resin layer 13 and the rear surface resin layer 14 cooperate to sandwich the heat generating sheet 2. The free surface of the front surface resin layer 13 forms a surface for contacting with the human body. The inner peripheral portion and the outer peripheral portion of the heating apparatus 12*c* form abutting surfaces between the front surface resin layer 13 and the rear surface resin layer 14. An electric wire 15 is disposed at the abutting surfaces. The abutting surfaces between the front surface resin layer 13 and the rear surface resin layer 14 near the electric wire 15 are fused to be bonded.

The heating apparatus 12c is fabricated by the following process. The electric wire 15 is embedded beforehand to half its diameter in the abutting surface of the rear surface resin layer 14 or the front surface resin layer 13. The heat generating sheet 2 is bonded to the front surface resin layer 13. The heat generating sheet 2 is sandwiched by the front surface resin layer 13 and the rear surface resin layer 14. The front surface resin layer 13 and the rear surface resin layer 14 are abutted together at the inner peripheral portion and the outer peripheral portion of the heating apparatus 12c. A predetermined voltage is applied between a pair of terminals 16 formed at the opposite ends of the electric wire 15 to energize the electric wire 15 and thereby fuse and bond the abutting surfaces between the front surface resin layer 13 and the rear surface resin layer 14.

In the process 3, since the bonded surfaces can be easily re-fused by energizing the electric wire 15, the front surface resin layer 13 can be removed from the rear surface resin layer 14 to enable removal of the heat generating sheet 2 from the heating apparatus 12c. Thus, reuse of the heat generating sheet 2 is expedited.

(4) Process 4

Figure 12:
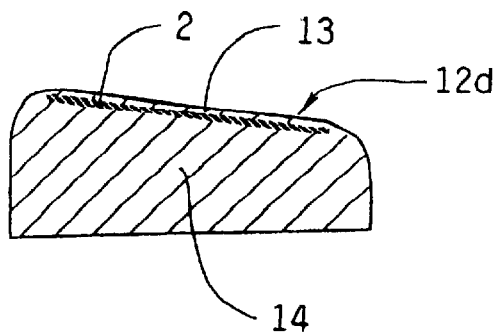
FIG. 12 is a sectional view of a heating apparatus in accordance with a preferred embodiment of the present invention which is embodied as a heating toilet seat.

As shown in FIG. 12, in a heating apparatus 12d which is embodied as a heating toilet seat, the front surface resin layer 13 and the rear surface resin layer 14 are fused into an integral body.

Figure 13:
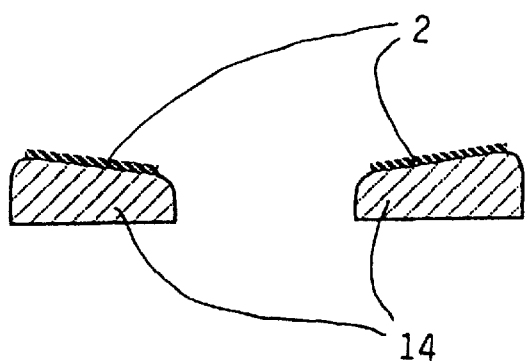
FIG. 13 is a sectional view of the heating apparatus of FIG. 12 showing the fabrication process of the heating apparatus.
Figure 14:
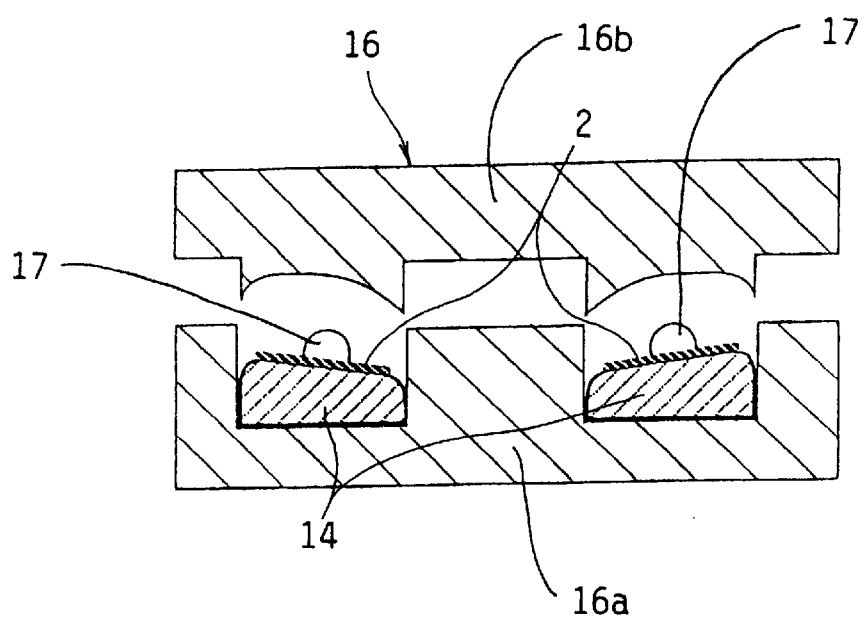
FIG. 14 is a sectional view of the heating apparatus of FIG. 12 and molds showing the fabrication process of the heating apparatus.

The heating apparatus 12d is fabricated by the following process. As shown in FIG. 13, the heat generating sheet 2 is placed on the premolded rear surface resin layer 14 to be bonded to the premolded rear surface resin layer 14. As shown in FIG. 14, the premolded rear surface resin layer 14 carrying the heat generating sheet 2 is placed in the female mold 16a of a mold 16 for low pressure molding. Resin material 17 of the front surface resin layer 13 is poured into the female mold 16a. The mold 16 is closed by the male mold 16b. Low pressure molding is carried out to form the heating apparatus 12d.

In the process 4, unity between the front surface resin layer 13 and the rear surface resin layer 14 increases and the strength of the heating apparatus 12d against external forces increases. Quick heating capability of the heating apparatus 12d increases because adherence of the heat generating sheet 2 to the front resin layer 13 increases. Low pressure molding protects the heat generating sheet 2 from damage during the molding operation.

It is possible to place the heat generating sheet 2 on the premolded front surface resin layer 13, bond the heat generating sheet 2 to the premolded front surface resin layer 13, place the premolded front surface resin layer 13 carrying the heat generating sheet 2 in the male mold 16b of the mold 16 for low pressure molding, pour the material 17 of the rear surface resin layer 14 into the male mold 16b, close the mold 16 by the female mold 16a, and carry out the low pressure molding to form the heating apparatus 12d. In this case, the mold 16 is used upside down.

Figure 15:
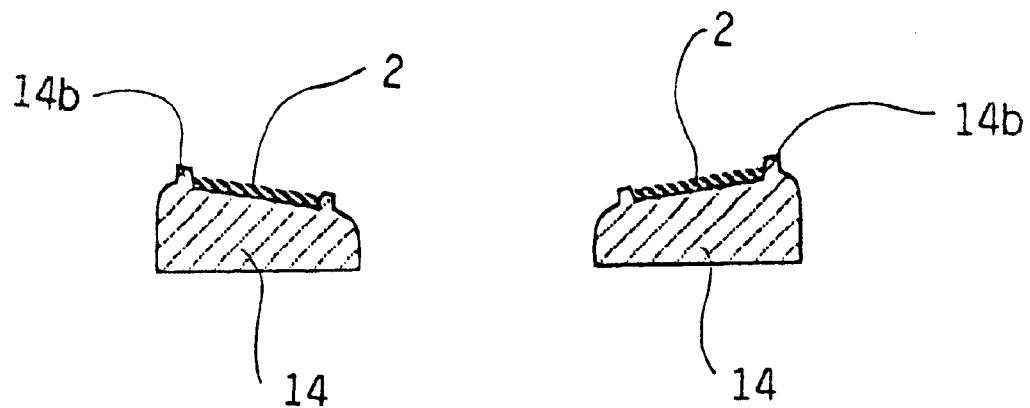
FIG. 15 is a sectional view of the heating apparatus of FIG. 12 showing another fabrication process of the heating apparatus.

In the process 4, the premolded rear surface resin layer 14 may be provided with projections 14b for immobilizing the heat generating sheet 2 as shown in FIG. 15. Thus, the heat generating sheet 2 is kept from sliding and crumpling during the molding operation. When the heat generating sheet 2 is placed on the premolded front surface layer 13, the front surface layer 13 may be provided with the same projections as projections 14b.

Figure 16:
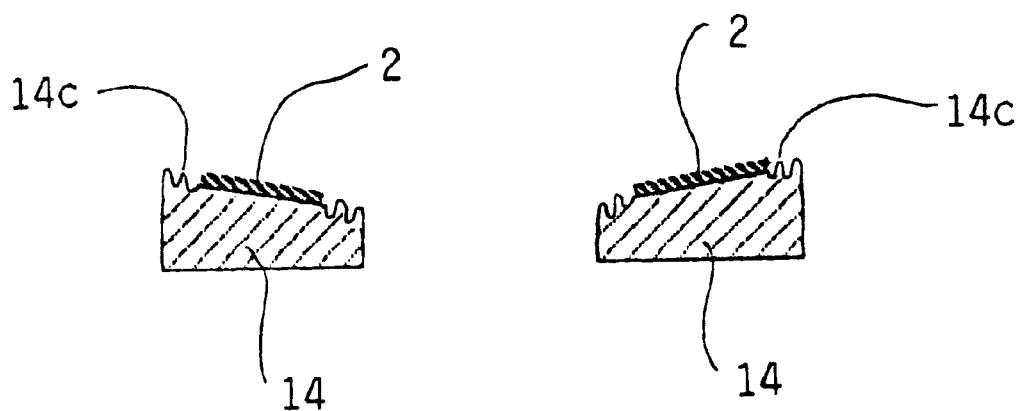
FIG. 16 is a sectional view of the heating apparatus of FIG. 12 showing another fabrication process of the heating apparatus.

In the process 4, the premolded rear surface resin layer 14 may be provided with irregularities or grooves 14c in the surface receiving the heat generating sheet 2 as shown in FIG. 16. Thus, the front surface resin layer 13 intrudes into the irregularities or grooves 14c to be firmly united with the rear surface resin layer 14 as an integral body. Thus, the strength of the heating apparatus 12d against external forces increases.

(5) Process 5

Figure 17:
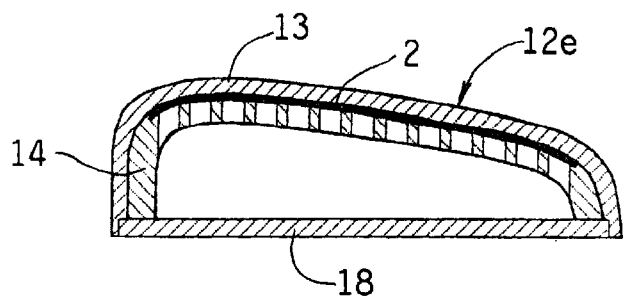
FIG. 17 is a sectional view of a heating apparatus in accordance with a preferred embodiment of the present invention which is embodied as a heating toilet seat.

As shown in FIG. 17, a heating apparatus 12e which is embodied as a heating toilet seat has a front surface resin layer 13, a heat generating sheet 2, a rear surface resin layer 14 which cooperates with the front surface resin layer 13 to sandwich the heat generating sheet 2 and a bottom cover 18. The rear surface resin layer 14 is honeycombed. A void space is formed between the rear surface resin layer 14 and the bottom cover 18.

Figure 18:
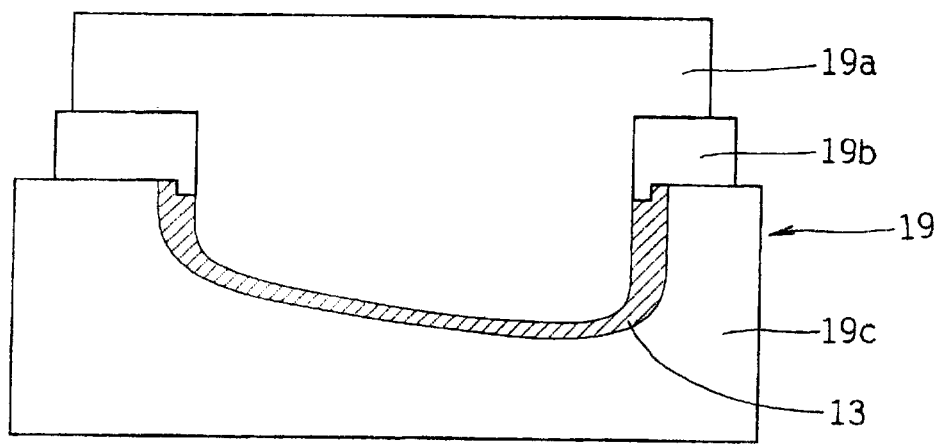
FIGS. 18(a) and 18(b) are sectional views of the heating apparatus of FIG. 17 and molds showing the fabrication process of the heating apparatus.
Figure 18:
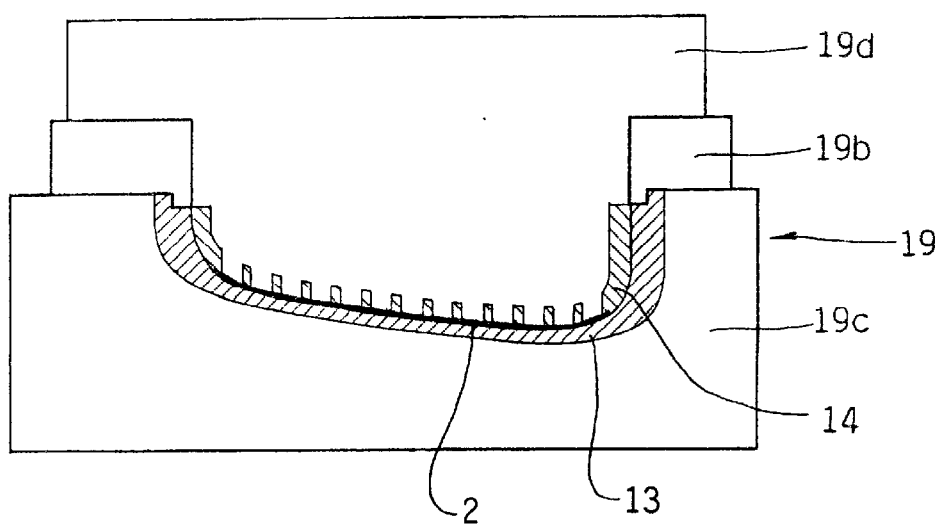

The heating apparatus 12e is fabricated by the following process. As shown in FIG. 18(a), the front surface resin layer 13 is low pressure molded by a mold 19 for low pressure molding comprising a male mold 19a, a middle mold 19b and a female mold 19c. The male mold 19a is removed. The front surface resin layer 13 is held in the female mold 19c. The front surface resin layer 13 is kept from shrinking and warping by the middle mold 19b. As shown in FIG. 18(b), the heat generating sheet 2 is placed on and bonded to the front surface resin layer 13. Resin material of the rear surface resin layer 14 is poured into the female mold 19c. The mold 19 is closed by a male mole 19d. Low pressure molding is carried out to mold the rear surface resin layer 14 with the front surface resin layer 13, thereby uniting them into an integral body. The molded body is removed from the mold 19. A premolded bottom cover 18 is attached to the molded body.

In the process 5, the same effects as in the process 4 can be obtained. In the process 5, the front surface resin layer 13, the heat generating sheet 2 and the rear surface resin layer 14 can be united into an integral body by a continuous series of processes. Thus, the trouble of transferring partially fabricated items such as the premolded front surface resin layer 13, the premolded rear surface resin layer 14, etc., and placing them in the mold can be avoided. The void space between the rear surface resin layer 14 and the bottom cover 18 is used as a wiring space as well as contributes to lighten the heating apparatus 12e.

It is possible to mold the rear surface resin layer 14 first and hold it in the mold, then mold the front surface resin layer 13 with the rear surface resin layer 14, thereby uniting them into an integral body.

(6) Process 6

Figure 19:
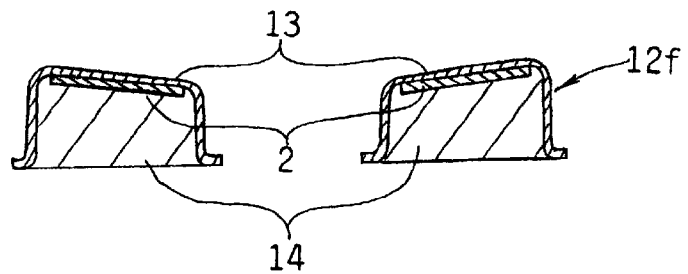
FIG. 19 is a sectional view of a heating apparatus in accordance with a preferred embodiment of the present invention which is embodied as a heating toilet seat.

As shown in FIG. 19, a heating apparatus 12f which is embodied as a heating toilet seat has a front surface resin layer 13, a heat generating sheet 2 and a rear surface resin layer 14 which cooperates with the front surface resin layer 13 to sandwich the heat generating sheet 2.

Figure 20:
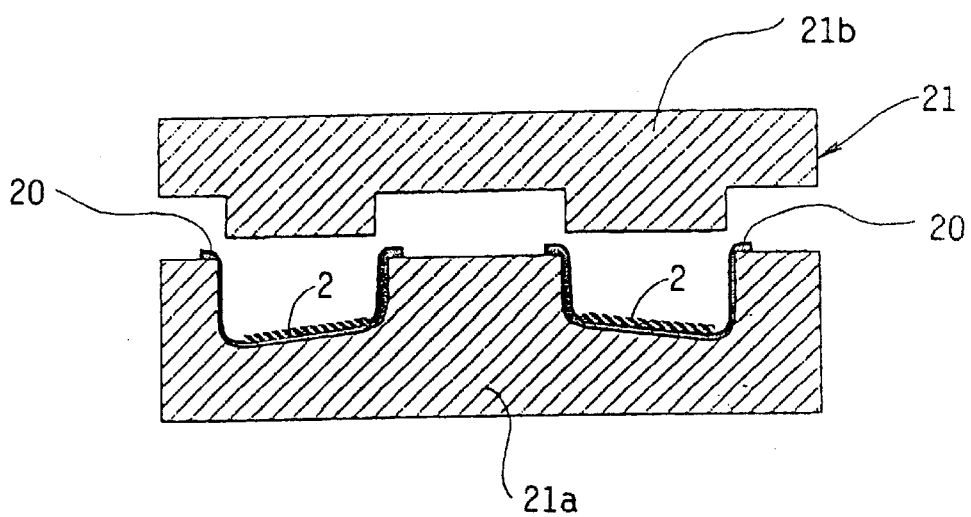
FIGS. 20(a) and 20(b) are sectional views of the heating apparatus of FIG. 19 and molds showing the fabrication process of the heating apparatus.
Figure 20:
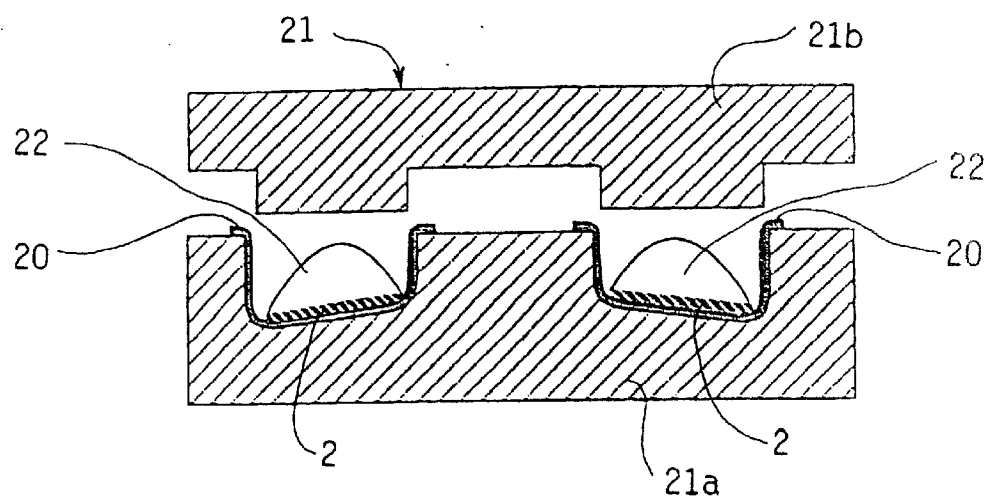
Figure 2:
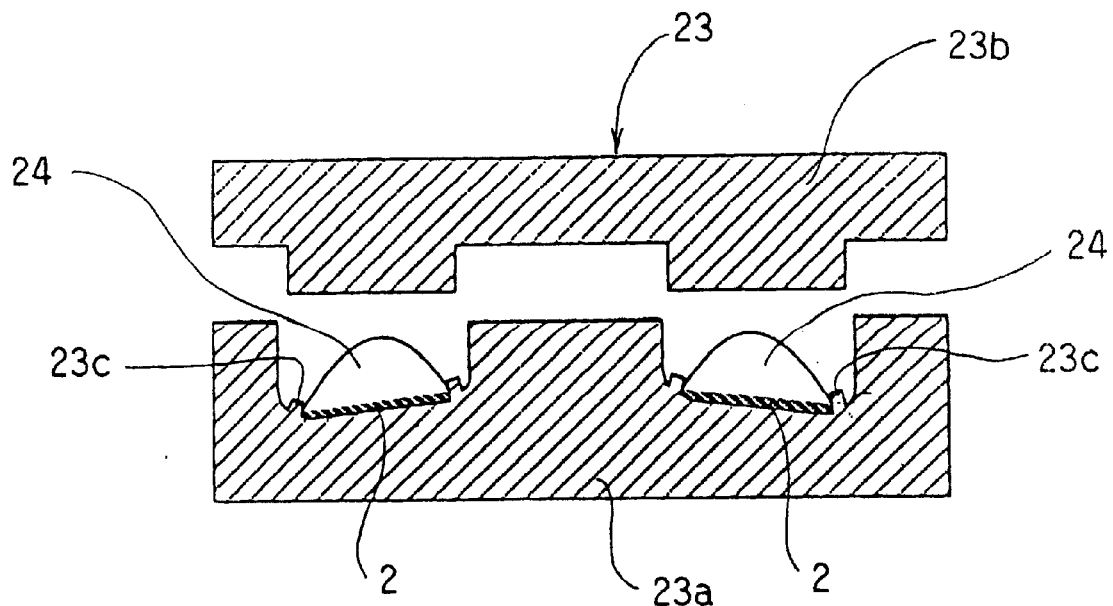
Figure 2:
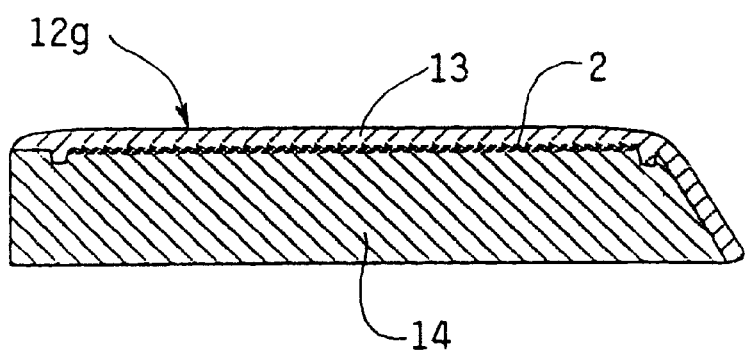

The heating apparatus 12f is fabricated by the following process. As shown in FIG. 20(a), a resin film 20 which forms the front surface resin layer 13 is vacuum attracted to a female mold 21a of a mold 21 for low pressure molding. The heat generating sheet 2 is placed on and bonded to the resin film 20. As shown in FIG. 20(b), resin material of the rear surface resin layer 14 is poured into the female mold 21a. The mold 21 is closed by a male mold 21b. Low pressure molding is carried out to form the heating apparatus 12f.

In the process 6, the same effects as in the process 4 can be obtained. In the process 6, the distribution of the thickness of the front surface resin layer 13 can be made even and the the thickness of the front surface resin layer 13 can be made small. When the distribution of the thickness of the front surface resin layer 13 is even, the temperature distribution of the free surface of the front surface resin layer 13 which forms the surface for contacting with the human body is even. Thus, the comfort of the heating apparatus 12f is enhanced. When the thickness of the front surface resin layer 13 is small, the quantity of infrared radiation passing through the front surface resin layer 13 increases and the quick heating capability of the heating apparatus 12f increases.

(7) Process 7

As shown in FIG. 21, a heating apparatus 12g which is embodied as a heating toilet seat has a front surface resin layer 13, a heat generating sheet 2 and a rear surface resin layer 14 which cooperates with the front surface resin layer 13 to sandwich the heat generating sheet 2.

The heating apparatus 12g is fabricated by the following process. As shown in FIG. 22, the heat generating sheet 2 is placed on a female mold 23a of a mold 23 for low pressure molding. Resin material of the rear surface resin layer 14 is poured into the female mold 23a. The mold 23 is closed by a male mold 23b. Low pressure molding is carried out to mold the rear surface resin layer 14 with the heat generating sheet 2 thereby uniting them into an integral body. The rear surface resin layer 14 carrying the heat generating sheet 2 is placed in another mold for low pressure molding. This mold is not shown in the FIG. 22. Resin material of the front surface resin layer 13 is poured into the mold. Low pressure molding is carried out to form the heating apparatus 12g.

In the process 7, unity between the front surface resin layer 13 and the rear surface resin layer 14 increases and the strength of the heating apparatus 12g against external forces increases. The quick heating capability of the heating apparatus 12g increases because adherence of the heat generating sheet 2 to the front resin layer 13 increases.

It is possible to mold the front surface resin layer 13 with the heat generating sheet 2 first, then mold the rear surface resin layer 14 with the front surface resin layer 13, thereby uniting them into an integral body.

In the process 7, the female mold 23a may be provided with projections 23c for immobilizing the heat generating sheet 2 as shown in FIG. 22. Thus, the heat generating sheet 2 is kept from sliding and crumpling during the molding operation.

In the heating apparatuses 12a to 12g, the heat generating sheet 2 may be given the same color as the front surface resin layer 13. Thus, the heat generating sheet 2 cannot be seen through and users of the heating apparatuses 12a to 12g do not feel uneasy even if the front surface resin layer 13 is light colored.

Figure 23:
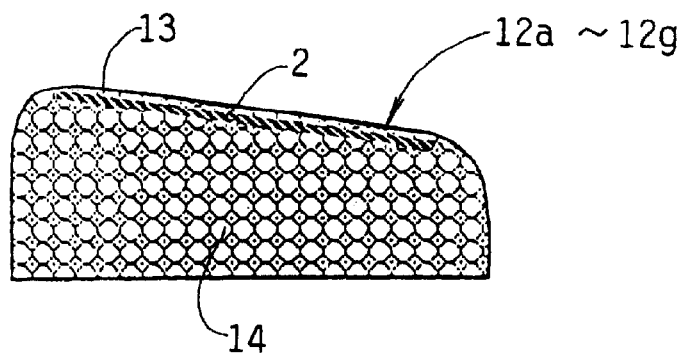
FIG. 23 is a sectional view of a heating apparatus in accordance with a preferred embodiment of the present invention which is embodied as a heating toilet seat.

In the heating apparatuses 12a to 12g, the front surface resin layer 13 and/or the rear surface resin layer 14 may be foamed resin layers as shown in FIG. 23. By this, the heating apparatuses 12a to 12g become flexible and the comfort of the heating apparatuses 12a to 12g is enhanced.

Figure 24:
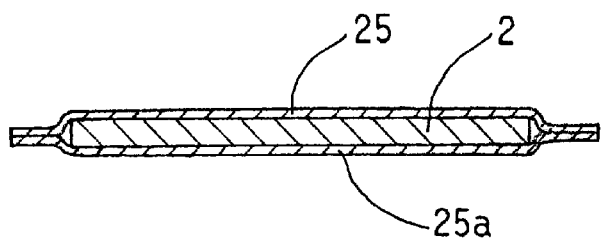
FIG. 24 is a sectional view of a heat generating sheet wrapped with a resin film.

In the heating apparatuses 12a to 12g, the heat generating sheet 2 may be wrapped with a resin film 25 beforehand as shown in FIG. 24. In this case, the heat generating sheet 2 is protected from damage when the front surface resin layer 13, the heat generating sheet 2 and the rear surface resin layer 14 are united into an integral body and the manufacturing efficiency of the heating apparatuses 12a to 12g increases because handling of the heat generating sheet 2 becomes easy.

When the heat generating sheet 2 is wrapped with a resin film 25 beforehand, the portion of the resin film 25 opposing the rear surface resin layer 14 may be an infrared reflection film 25a as shown in FIG. 24. In this case, the infrared radiation from the surface of the generating sheet 2 directed away from the human body is reflected toward the human body by the infrared reflection film 25a, thereby contributing to temperature increase of the human body. Thus, the quick heating capability of the heat radiators 12a to 12g increases.

Figure 25:
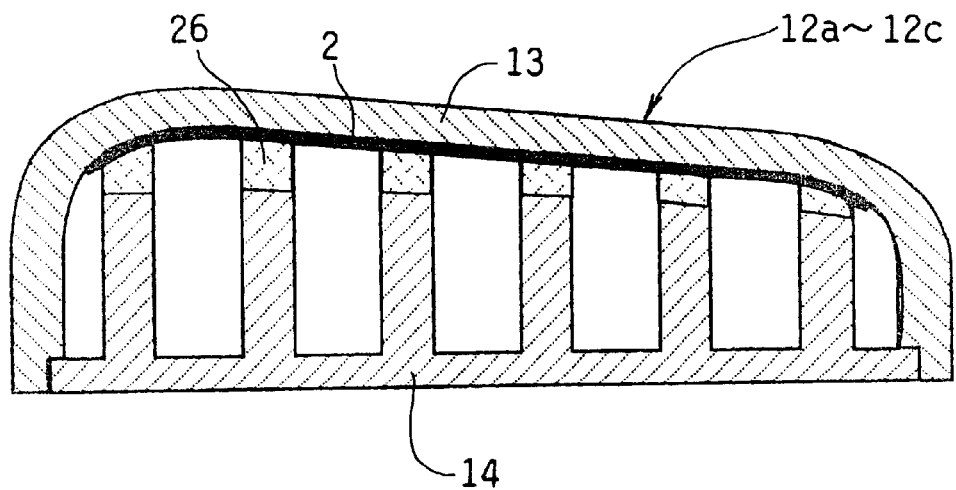
FIG. 25 is a sectional view of a heating apparatus in accordance with a preferred embodiment of the present invention which is embodied as a heating toilet seat.
Figure 2:
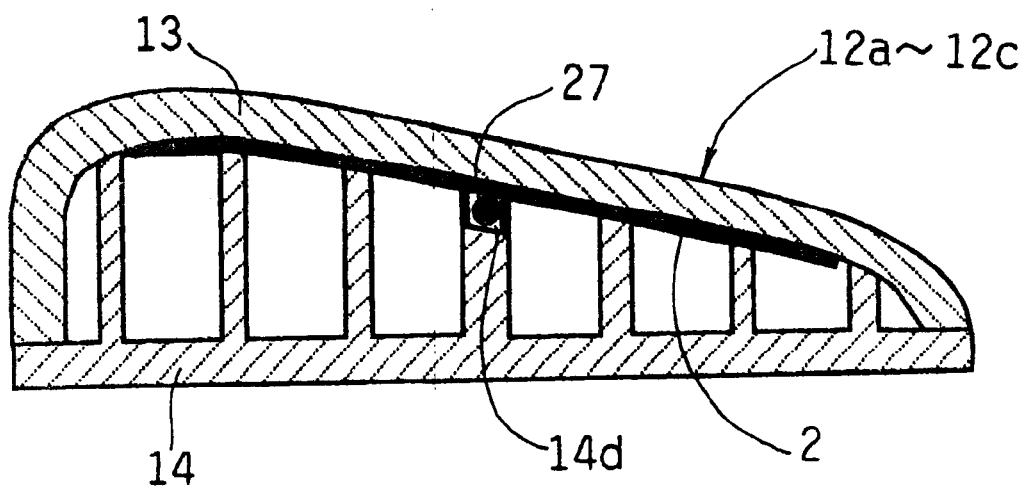
Figure 2:
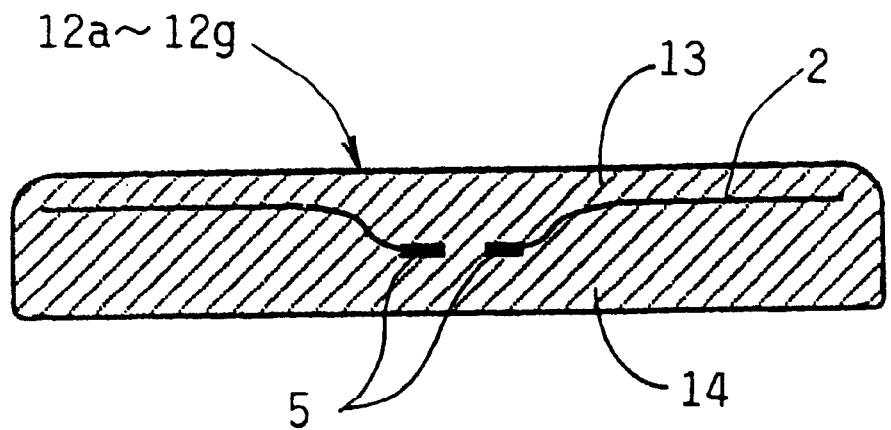

In the heating apparatuses 12a to 12c, a cushioning layer 26 may be sandwiched between the rear surface resin layer 14 and the heat generating sheet 2 as shown in FIG. 25. When the front surface resin layer 13, the heat generating sheet 2 and the rear surface resin layer 14 are united into an integral body by any one of the processes 1 to 3, there is a possibility of their not being sufficiently united into an integral body because of size mismatch between the front surface resin layer 13 and the rear surface resin layer 14 caused by manufacturing error. However, if a cushioning layer 26 is sandwiched between the rear surface resin layer 14 and the heat generating sheet 2, any size mismatch between the front surface resin layer 13 and the rear surface resin layer 14 is absorbed by the cushioning layer 26. Thus, sufficient unity can be obtained.

When a cushioning layer 26 is sandwiched between the rear surface resin layer 14 and the heat generating sheet 2 in the heating apparatuses 12a to 12c, the cushioning layer 26 may be integrally molded with the rear surface resin layer 14. By this, the trouble of inserting the cushioning layer 26 between the heat generating sheet 2 and the rear surface resin layer 14 can be avoided when the front surface resin layer 13, the heat generating sheet 2 and the rear surface resin layer 14 are united into an integral body. Thus, the manufacturing efficiency of the heating apparatuses 12a to 12c increases.

When a cushioning layer 26 is sandwiched between the rear surface resin layer 14 and the heat generating sheet 2 in the heating apparatuses 12a to 12c, the cushioning layer 26 may be a heat insulator. In this case, the heat generated by the heat generating sheet 2 is not absorbed by the cushioning layer 26, the heating efficiency of the heat generating sheet 2 increases and the quick heating capability of the heating apparatuses 12a to 12c increases.

As in the heating apparatuses 12a to 12c and 12e, the rear surface resin layer 14 may be honeycombed. In this case, the weights of the heating apparatuses 12a to 12c and 12e are reduced.

In the heating apparatuses 12a to 12c, the rear surface resin layer 14 may be provided with a hollow 14d wherein a heat sensor 27 is received as shown in FIG. 26. In this case, the heat generating sheet 2 can be precisely controlled and the heating apparatuses 12a to 12c can be precisely controlled.

If the temperature distribution of the heat generating sheet 2 is uneven in the heating apparatuses 12a to 12g, the front surface resin layer 13 facing the higher temperature portion of the heat generating sheet 2 may be made thick and the front surface resin layer 13 facing the lower temperature portion of the heat generating sheet 2 may be made thin. By this, temperature distribution of the free surface of the front surface resin layer 13 which forms the surface for contacting with the human body becomes even and the comfort of the heating apparatuses 12a to 12g is enhanced. In the example shown in FIG. 27, the portion of the front surface resin layer 13 facing the electrodes 5 is made thicker than other portions taking into account that the temperature of the electrodes 5 is higher than that of other portions. If the horseshoe-shaped heat generating sheet 2 is used as shown in FIGS. 7 and 10, the thickness of the front surface resin layer 13 may be gradually decreased from the portion opposing the inner periphery of the heat generating sheet 2 to the portion opposing the outer periphery of the heat generating sheet 2 because the distance between the pair of electrodes 5 increases from the inner periphery to the outer periphery and the temperature of the heat generating sheet 2 decreases from the inner periphery to the outer periphery. When the portion of the front surface resin layer 13 facing the higher temperature portion of the heat generating sheet 2 is made thick and the portion of the front surface resin layer 13 facing the lower temperature portion of the heat generating sheet 2 is made thin, the temperature distribution of the free surface of the front surface resin layer 13 which forms the surface for contacting with the human body becomes even. Thus, the comfort of the heating apparatuses 12a to 12g is enhanced.

Figure 29:
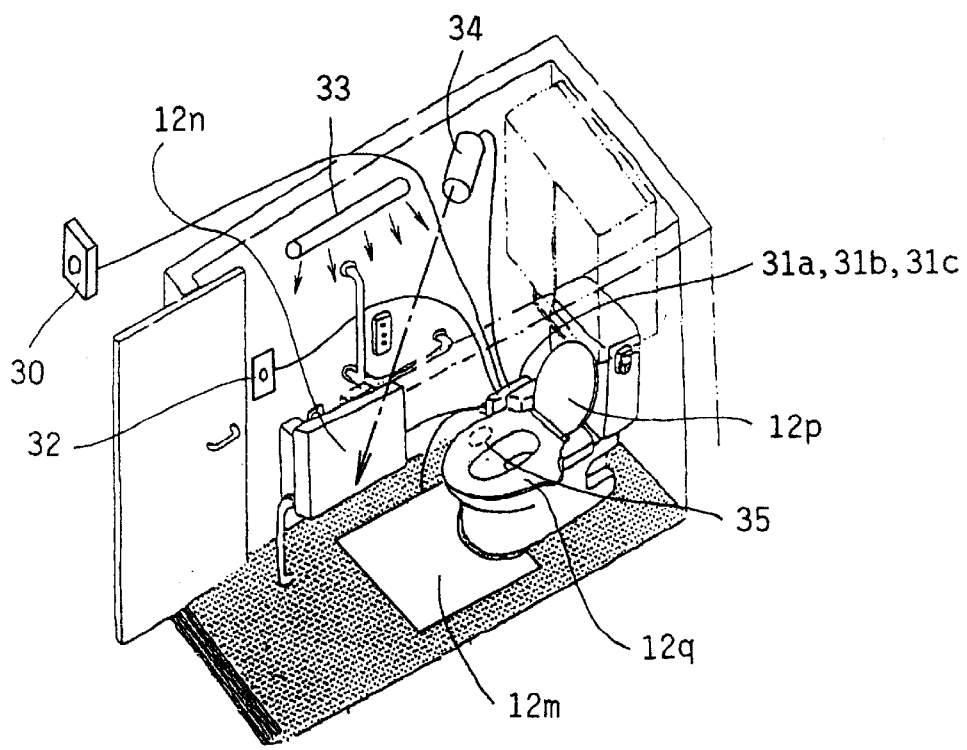
FIG. 29 is a bird's-eye view of a toilet wherein heating apparatuses in accordance with preferred embodiments of the present invention are installed.
Figure 28:
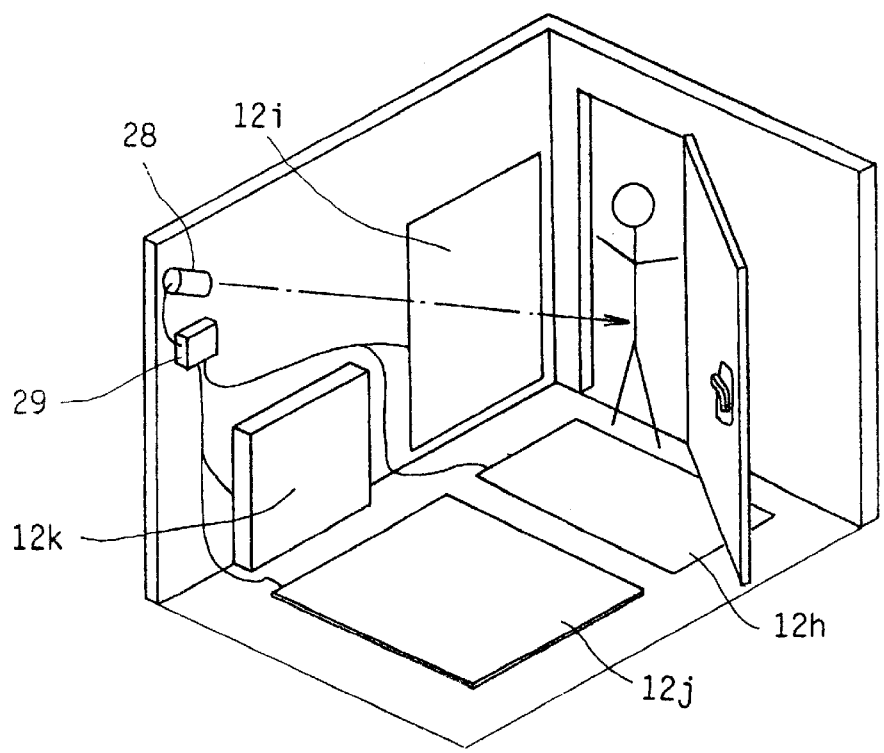
FIG. 28 is a bird's-eye view of a room wherein heating apparatuses in accordance with preferred embodiments of the present invention are installed.

The heating apparatus 12 having the heat radiator 1 can be applied to various kinds of heating apparatuses such as room heating apparatuses, toilet heating apparatuses, etc. As shown in FIG. 28, examples of room heating apparatuses include a floor heating panel 12h, a wall heating panel 12i, a heating carpet 12j, a heating panel 12k, etc. As shown in FIG. 29, examples of toilet heating apparatuses include a heating toilet mat 12m, a heating panel 12n, a heating toilet seat cover 12p, a heating toilet seat 12q, etc. The heating apparatus 12 in accordance with the present invention wherein the heat generating sheet 2 is flexible and the front surface resin layer 13 and the rear surface resin layer 14 are made of flexible material can be applied to a heating robe, winter clothes, a chair seat, a chair backrest, a chair armrest, etc.

A room heating apparatus such as the heating panel 12h, the wall heating panel 12i, the heating carpet 12j, the heating panel 12k, etc. shown in FIG. 28 may further comprise a human body detecting apparatus 28 such as an infrared sensor, pyroelectric sensor, Doppler sensor, microwave sensor, $CO_2$ sensor, microphone sensor, etc. which can detect the presence of a person in a room and a heat source controller 29 which energizes the heat generating sheet 2 only when the human body detecting apparatus 28 detects the presence of a person. By this, the electric power consumption of the room heating apparatus is reduced because the room heating apparatus operates only when a person is present in the room.

A toilet heating apparatus such as the heating toilet mat 12m, the heating panel 12n, the heating toilet seat cover 12p, the heating toilet seat 12q, etc. shown in FIG. 29 may further comprise a heat source controller 31a which energizes the heat generating sheet 2 in accordance with a control signal from a control switch 30 disposed outside the toilet. Thus, the toilet heating apparatus can be started just before a person enters the toilet and stopped just after the person leaves the toilet. Thus, the toilet can be comfortably used and the electric power consumption of the toilet heating apparatus can be reduced.

A toilet heating apparatus such as the heating toilet mat 12m, the heating panel 12n, the heating toilet seat cover 12p, the heating toilet seat 12q, etc. shown in FIG. 29 may further comprise a heat source controller 31b which energizes the heat generating sheet 2 only when an electric lamp 33 in the toilet is switched on by a control switch 32 disposed in or outside the toilet. In an ordinary home, the electric lamp 33 in the toilet is switched on only when the toilet is used. Thus, the above described heat source controller 31b enables comfortable use of the toilet as well as reduction of electric power consumption of the toilet heating apparatus.

A toilet heating apparatus such as the heating toilet mat 12m, the heating panel 12n, the heating toilet seat cover 12p, the heating toilet seat 12q, etc. shown in FIG. 29 may further comprise a human body detecting apparatus 34 which can detect the presence of a person in a toilet and a heat source controller 31c which energizes the heat generating sheet 2 only when the human body detecting apparatus 34 detects the presence of a person. Thus, the electric power consumption of the toilet heating apparatus is reduced because the toilet heating apparatus operates only when a person is present in the toilet. The same apparatus as the human body detecting apparatus 28 shown in FIG. 28 may be used as the human body detecting apparatus 34. An apparatus for detecting the seating of a person on a toilet seat used in a bidet may be used as the human body detecting apparatus 34.

When the same apparatus as the human body detecting apparatus 28 shown in FIG. 28 is used as the human body detecting apparatus 34, the heat source controller 31c can be adapted to energize the heat generating sheet 2 a predetermined time after the human body detecting apparatus 34 detects a person. The human body detecting apparatus 34 detects a person just after the person enters the toilet. Around 10 to 20 seconds pass between the time a person enters the toilet and the time the person sits on the heating toilet seat 12q. Thus, even if the heat source controller 31c energizes the heat generating sheet 2 a predetermined time after the human body detecting apparatus 34 detects the presence of a person, some time is still available between the time the heat generating sheet 2 is energized and the time the person sits on the toilet heating seat 12q. The surface of the toilet heating apparatus for contacting with the human body can be reliably heated to an appropriate temperature during the available time because the toilet heating apparatus in accordance with the present invention is excellent in quick heating capability. A toilet heating apparatus such as the heating toilet mat 12m, the heating panel 12n, the heating toilet seat cover 12p, the heating toilet seat 12q, etc. achieves its warming effect by making contact with the person sitting on the heating toilet seat 12q or by being present very close to the person sitting on the heating toilet seat 12q. Thus, the comfort of the toilet heating apparatus is not impaired so long as the temperature of the surface of the toilet heating apparatus for contacting with the human body is raised to an appropriate level before the person sits on the heating toilet seat 12q. Thus, the electric power consumption of the toilet heating apparatus is reduced without impairing the comfort of the toilet heating apparatus owing to the delayed turnon of the toilet heating apparatus.

The heat source controller 31c may energize the heat generating sheet 2 at time T-t after the human body detecting apparatus 34 detects a person. T is the time between detection of the person by the human body detecting apparatus 34 and the seating of the person on the heating toilet seat 12q and t is the time from energizing of the heat generating sheet 2 to the completion of the temperature rise of the front surface resin layer 13 to a predetermined level. The comfort of the toilet heating apparatus is not impaired because the temperature of the surface of the toilet heating apparatus for contacting with the human body rises to an appropriate level before the person sits on the heating toilet seat 12q. Thus, the electric power consumption of the toilet heating apparatus is reduced without impairing the comfort of the toilet heating apparatus owing to the above-mentioned delayed turnon of the toilet heating apparatus.

Figure 30:
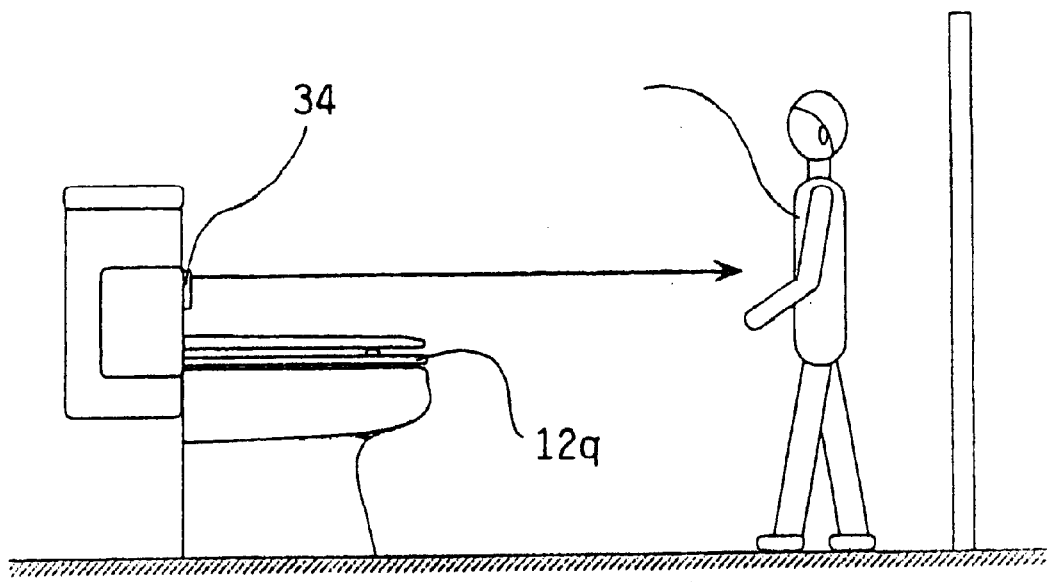
FIG. 30 is a sectional view of a toilet wherein heating apparatuses in accordance with preferred embodiments of the present invention are installed.

The human body detecting apparatus 34 may be one capable of detecting the distance between the human body detecting apparatus 34 and the person that is mounted on a flushing water tank disposed adjacent to the heating toilet seat 12q as shown in FIG. 30 and the heat source controller 31c may be one that energizes the heat generating sheet 2 when the distance between the human body detecting apparatus 34 and the person becomes a predetermined value. An automatic focusing sensor used for a camera can be used for the human body detecting apparatus 34 capable of detecting the distance to the person. Even if the toilet heating apparatus is turned on when the person reaches a point a predetermined distance from the heating toilet seat 12q, the temperature of the surface of the toilet heating apparatus for contacting with the human body can nevertheless be raised to an appropriate level because the toilet heating apparatus having the heat radiator 1 is excellent in quick heating capability. The comfort of the toilet heating apparatus is therefore not impaired. The electric power consumption of the toilet heating apparatus is reduced owing to the delayed turnon of the toilet heating apparatus.

Figure 31:
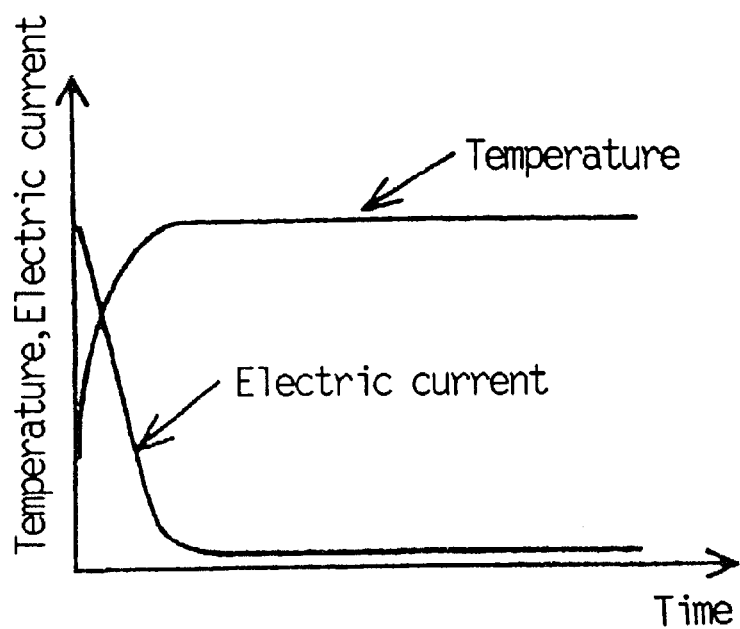
FIG. 31 is a diagram showing the relation between the electric current flowing through the heat generating sheet of a heating apparatus in accordance with a preferred embodiment of the present invention and the temperature of the heat generating sheet.

In a toilet heating apparatus such as the heating toilet mat 12m, the heating panel 12n, the heating toilet seat cover 12p, the heating toilet seat 12q, etc. shown in FIG. 29, the temperature coefficient of resistance of the heat generating sheet 2 may be positive. When the temperature coefficient of resistance of the heat generating sheet 2 is positive, the temperature of the energized heat generating sheet 2 asymptotically approaches a constant level as shown in FIG. 31, because the resistance of the heat generating sheet 2 increases and the electric current flowing through the heat heat generating sheet 2 decreases as the temperature of the heat generating sheet 2 increases. Thus, the toilet heating apparatus is prevented from overheating. If the constant temperature is set at a level near body temperature, the temperature of the surface of the toilet heating apparatus for contacting with the human body automatically rises to an appropriate level. A heating element made of the mixture of carbon particles and matrix resin has a positive temperature coefficient of resistance. When the heating element is energized, the carbon particles generate heat and the temperature of the heating element rises. When the temperature of the heating element rises, the matrix resin expands, the space between the carbon particles increases, the resistance of the heating element increases, the electric current in the heating element decreases and the temperature of the heating element drops. When the temperature of the heating element drops, the matrix resin contracts, the space between the carbon particles decreases, the resistance of the heating element decreases, the electric current in the heating element increases and the temperature of the heating element rises. The above described phenomenon is repeated to hold the temperature of the heating element at a constant level. A metal resistor also has a positive temperature coefficient of resistance.

In a toilet heating apparatus such as the heating toilet mat 12m, the heating panel 12n, the heating toilet seat cover 12p, the heating toilet seat 12q, etc. shown in FIG. 29, the heat source controller 31a, 31b or 31c can be adapted to variably control the electric power supply to the heat generating sheet 2. In this case, the toilet heating apparatus is prevented from overheating and also reliably heated to an appropriate temperature even if the environmental conditions such as room temperature, etc. have changed.

Figure 32:
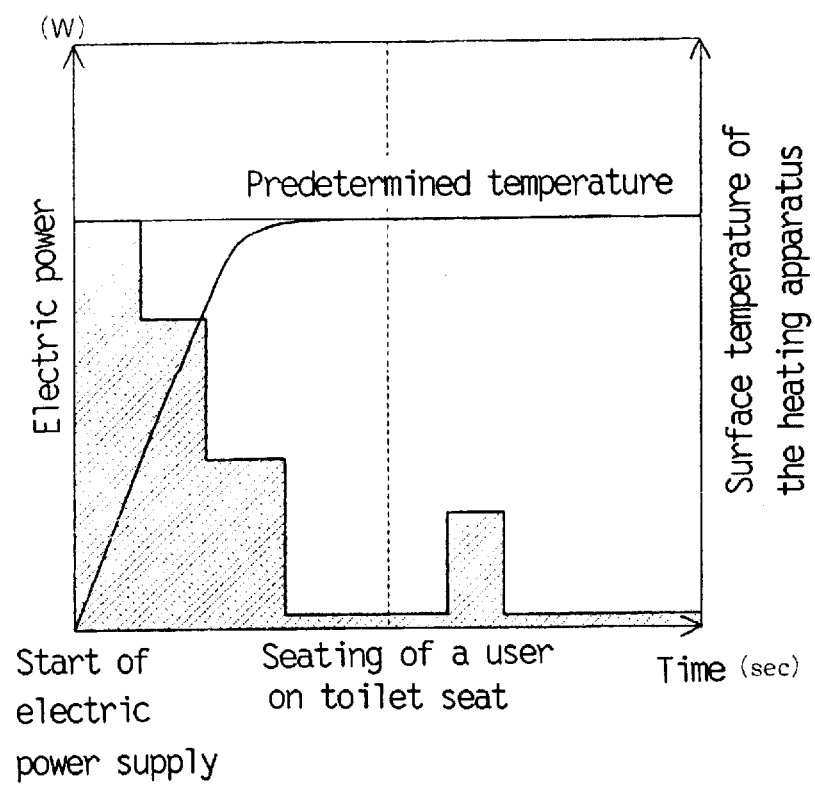
FIG. 32 is a diagram showing an example of a control sequence of the heating apparatus in accordance with a preferred embodiment of the present invention.

In a toilet heating apparatus such as the heating toilet mat 12m, the heating panel 12n, the heating toilet seat cover 12p, the heating toilet seat 12q, etc. shown in FIG. 29, the heat source controller 31a, 31b or 31c can be adapted to vary the electric power supply to the heat generating sheet 2 stepwise as shown in FIG. 32. By this, the increase rate of the temperature of the toilet heating apparatus increases and the toilet heating apparatus is prevented from overheating.

Figure 33:
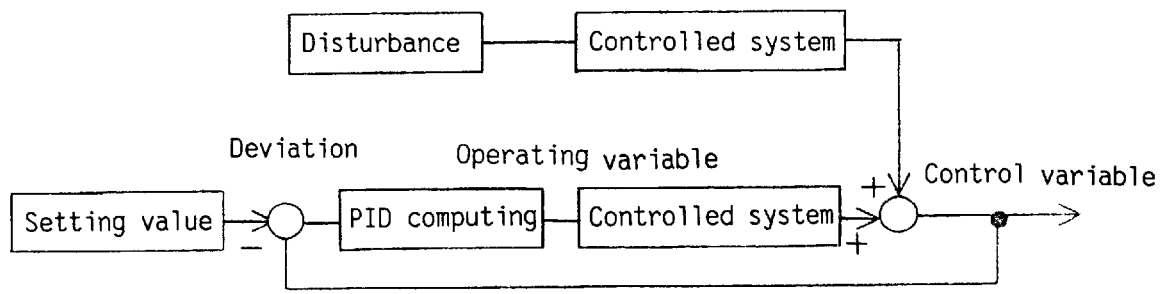
FIG. 33 is a block diagram showing an example of a control sequence of the heating apparatus in accordance with a preferred embodiment of the present invention.

In a toilet heating apparatus such as the heating toilet mat 12m, the heating panel 12n, the heating toilet seat cover 12p, the heating toilet seat 12q, etc. shown in FIG. 29, the heat source controller 31a, 31b or 31c can be adapted to determine the electric power supply to the heat generating sheet 2 by feedback control as shown in FIG. 33. In FIG. 33, the appropriate temperature of the surface of the toilet heating apparatus is the setting value, the present temperature of the surface of the toilet heating apparatus is the control variable and the difference between the setting value and the control variable is the deviation. PID computing is carried out corresponding to the deviation to determine the operating variable or the electric power supply to the heat generating sheet 2. The determined electric power is supplied to the controlled system or the heat generating sheet 2. Rapid fluctuation of ambient temperature, etc. affects the operating variable as the disturbance. P computing varies the operating variable proportionally to the deviation. I computing varies the operating variable proportionally to the time integral of the deviation. D computing varies the operating variable proportionally to the time differential of the deviation. PID computing combines these computings to determine the operating variable. PID computing enables quick and precise optimum control.

Figure 34:
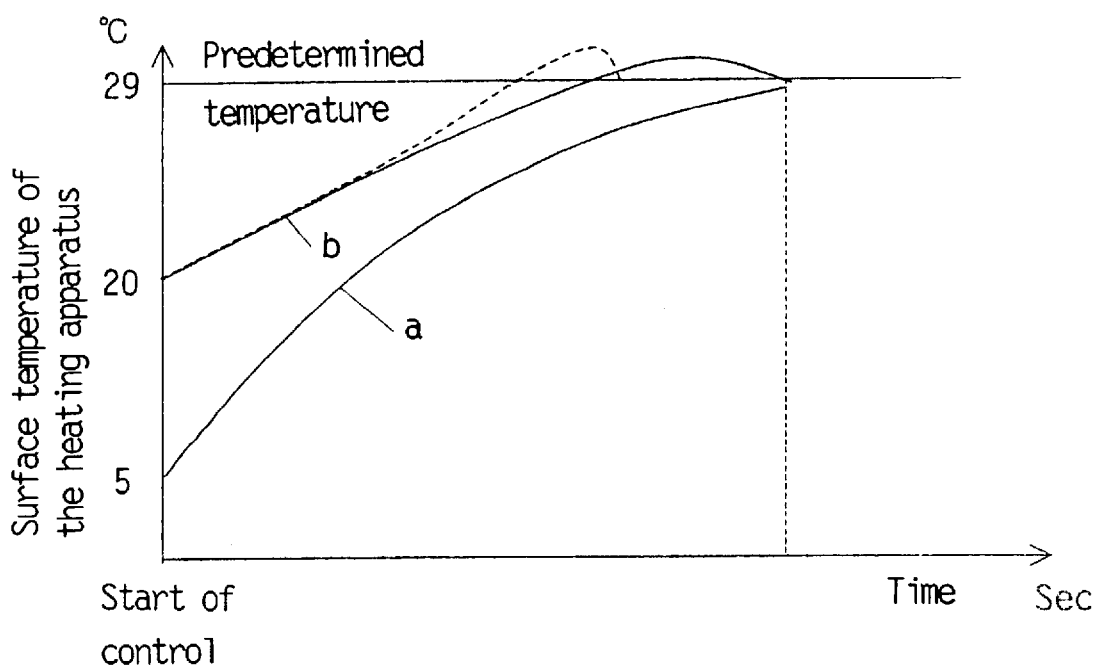
FIG. 34 is a diagram showing an example of a control sequence of the heating apparatus in accordance with a preferred embodiment of the present invention.

As shown in FIG. 34, D computing is omitted to achieve quick heating when the deviation is large at the start of the control(line a in FIG. 34). P computing is omitted to prevent overheating when the deviation is small at the start of the control(line b in FIG. 34). Usually D computing is omitted at the start of the control and started when the deviation becomes small to achieve quick heating.

The initial electric power supply in the control shown in FIG. 32 or the initial control constants in the control shown in FIG. 33 may be determined in accordance with the ambient temperature in the toilet. When the ambient temperature is low, the initial electric power supply is increased or the initial control constants are increased to enhance the quick heating capability of the toilet heating apparatus. When the ambient temperature is high, the initial electric power supply is decreased or the initial control constants are decreased to prevent the toilet heating apparatus from overheating.

Figure 35:
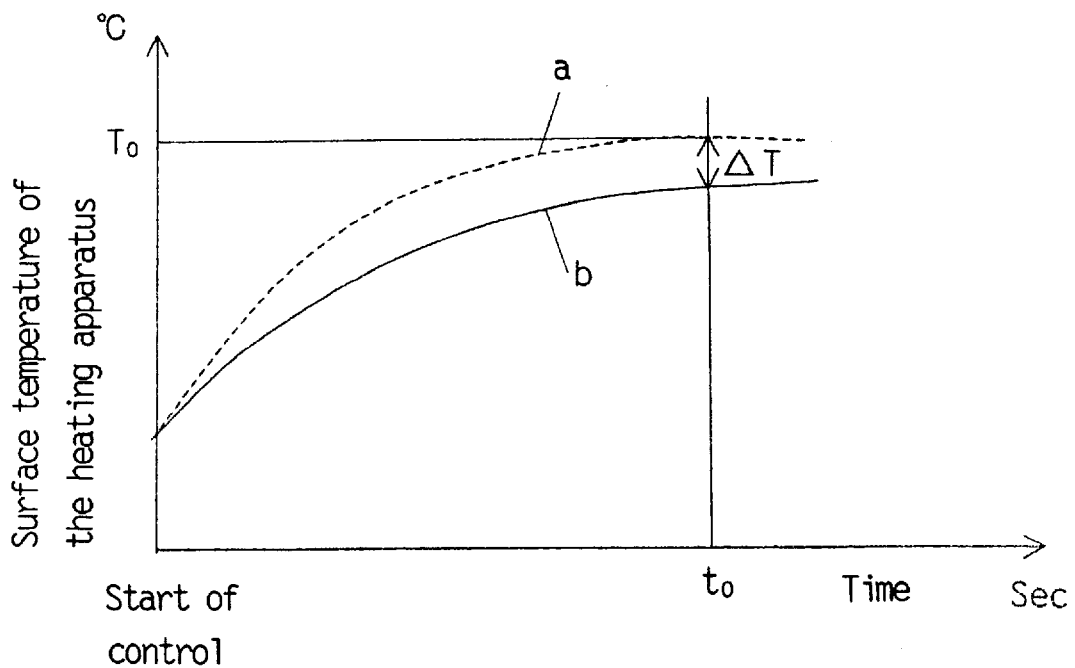
FIG. 35 is a diagram showing an example of a control sequence of the heating apparatus in accordance with a preferred embodiment of the present invention.

In a toilet heating apparatus such as the heating toilet mat 12m, the heating panel 12n, the heating toilet seat cover 12p, the heating toilet seat 12q, etc. shown in FIG. 29, the heat source controller 31a, 31b or 31c can be adapted to determine the electric power supply to the heat generating sheet 2 by learning control. When the toilet heating apparatus is shipped from the factory, constants of the control shown in FIG. 32 or 33 are set to raise the surface temperature of the toilet heating apparatus to a predetermined level in a predetermined time. The surface temperature of the toilet heating apparatus should rise to $T_0$, $t_0$ after the start of the control as shown by line a in FIG. 35. Because of the deviation from standard performance of the heat generating sheet 2, deviation from standard thickness of the front surface resin layer 13, etc., however, the surface temperature of the toilet heating apparatus sometimes rises only to $T_0-\Delta T$, $t_0$ after the start of the control, as shown by line b in FIG. 35. In this case, the constants of the control are corrected corresponding to the deviation $\Delta T$ by means of the learning control to correct the electric power supply to the heat generating sheet 2. Thus, the toilet heating apparatus can exhibit the expected performance from the next operation.

A toilet heating apparatus such as the heating toilet mat 12m, the heating panel 12n, the heating toilet seat cover 12p, the heating toilet seat 12q, etc. shown in FIG. 29, can be provided with a detecting apparatus 35 which detects the seating of a person on the heating toilet seat 12q, and the heat source controller 31a, 31b or 31c can be adapted to decrease the electric power supply to the heat generating sheet 2 when the detecting apparatus 35 detects the seating of a person on the heating toilet seat 12q. A load cell can be used as the detecting apparatus 35. This feature can be used in an arrangement in which, after a person sits on the heating toilet seat 12q, the person's feet contact the toilet heating mat 12m placed near the heating toilet seat 12q, buttocks contact the heating toilet seat 12q and the back contacts the heating toilet seat cover 12p to keep them warm. The heating panel 12n can also be located to be very close to the person to be warmed. By this, the comfort of the toilet heating apparatus is not impaired even if the electric power supply to the toilet heating apparatus is reduced after the person sits on the heating toilet seat 12q. Thus, the electric power consumption of the toilet heating apparatus is reduced by reducing of the power supply to the toilet heating apparatus.

INDUSTRIAL APPLICABILITY OF THE INVENTION

The present invention provides a heating apparatus which has a surface for contacting with the human body and is excellent in quick heating capability.

What is claimed is:

1. A heat radiator for emitting infrared radiation to the human body, comprising:
   a heat source energized to emit infrared radiation, whose penetration depth into the human body is to near warmth sensing points of the human body; and
   an insulator covering the surface of the heat source directed toward the human body;
   wherein the free surface of the insulator forms a surface for contacting with the human body and the thickness of the insulator is less than the penetration depth of the infrared radiation into the insulator.

2. A heat radiator of claim 1, wherein the insulator is made of polyester resin or styrene resin.

3. A heat radiator of claim 1, wherein the insulator adheres closely to the heat source.

4. A heat radiator of claim 3, wherein the heat source is a porous heat generating sheet.

5. A heat radiator of claim 4, wherein the porous heat generating sheet is a mixed paper of carbon fibers and natural pulp fibers, and the carbon fibers are surrounded by void spaces.

6. A heat radiator of claim 5, wherein the void ratio of the mixed paper is equal to or greater than 60 volume %.

7. A heat radiator of claim 1, further comprising an infrared reflector facing the surface of the heat source directed away from the human body.

8. A heating apparatus having a heat radiator of any of claims 1 to 7, comprising:
   a front surface resin layer to be directed toward the human body; and
   a rear surface resin layer;
   wherein the front surface resin layer forms the insulator of the heat radiator covering the surface of the heat source directed toward the human body, and the front surface resin layer and the rear surface resin layer cooperate to sandwich the heat source of the heat radiator.

9. A heating apparatus of claim 8, wherein the front surface resin layer, the heat source and the rear surface resin layer are united into an integral body by the process comprising the steps of:
   inserting projections extending from the front surface resin layer and penetrating through the heat source into penetration holes formed in the rear surface resin layer; and
   heat fusing the end portions of the projections to form swellings.

10. A heating apparatus of claim 8, wherein the front surface resin layer, the heat source and the rear surface resin layer are united into an integral body by the process of inserting projections extending from the front surface resin layer, penetrating through the heat source and being provided with swellings at their ends into penetration holes formed in the rear surface resin layer.

11. A heating apparatus of claim 8, wherein the front surface resin layer, the heat source and the rear surface resin layer are united into an integral body by the process comprising the steps of:
   abutting the front surface resin layer against the rear surface resin layer; and
   energizing an electric wire embedded beforehand in the abutting surface of the rear surface resin layer or the front surface resin layer to fuse and bond the abutting surfaces.

12. A heating apparatus of claim 8, wherein the front surface resin layer, the heat source and the rear surface resin layer are united into an integral body by the process comprising the steps of:
   placing the heat source on the premolded front surface resin layer or the premolded rear surface resin layer;
   placing the premolded front surface resin layer carrying the heat source or the premolded rear surface resin layer carrying the heat source in a mold for low pressure molding;
   pouring resin material of the rear surface resin layer or the front surface resin layer into the mold; and
   closing the mold to carry out low pressure molding.

13. A heating apparatus of claim 12, wherein the premolded front surface resin layer or the premolded rear surface resin layer is provided with projections for immobilizing the heat source.

14. A heating apparatus of claim 12, wherein the premolded rear surface resin layer is provided with irregularities or grooves in the surface receiving the heat source.

15. A heating apparatus of claim 8, wherein the front surface resin layer, the heat source and the rear surface resin layer are united into an integral body by the process comprising the steps of:
   molding the front surface resin layer or the rear surface resin layer;
   holding the molded front surface resin layer or the molded rear surface resin layer in the mold;
   placing the heat source on the front surface resin layer or the rear surface resin layer;
   pouring resin material of the rear surface resin layer or the front surface resin layer into the mold; and
   closing the mold to carry out low pressure molding.

16. A heating apparatus of claim 8, wherein the front surface resin layer, the heat source and the rear surface resin layer are united into an integral body by the process comprising the steps of:

vacuum attracting a resin film to a mold for low pressure molding;

placing the heat source on the resin film;

pouring resin material of the rear surface resin layer into the mold; and closing the mold to carry out low pressure molding.

17. A heating apparatus of claim 8, wherein the front surface resin layer, the heat source and the rear surface resin layer are united into an integral body by the process comprising the steps of:

placing the heat source on a first mold for low pressure molding;

pouring resin material of the front surface resin layer or the rear surface resin layer into the mold;

closing the mold to carry out low pressure molding to unite the front surface resin layer or the rear surface resin layer and the heat source into an integral body;

placing the front surface resin layer united with the heat source or the rear surface resin layer united with the heat source in a second mold for low pressure molding;

pouring resin material of the rear surface resin layer or the front surface resin layer into the mold; and closing the mold to carry out low pressure molding.

18. A heating apparatus of claim 17, wherein the first mold for low pressure molding is provided with projections for immobilizing the heat source.

19. A heating apparatus of claim 8, wherein the heat source is given the same color as the front surface resin layer.

20. A heating apparatus of claim 8, wherein the front surface resin layer and/or the rear surface resin layer are foamed resin layers.

21. A heating apparatus of claim 8, wherein the heat source is wrapped with a resin film beforehand.

22. A heating apparatus of claim 21, wherein the portion of the resin film opposing the rear surface resin layer is an infrared reflector.

23. A heating apparatus of any of claims 9 to 11, wherein a cushioning layer is sandwiched between the rear surface resin layer and the heat source.

24. A heating apparatus of claim 23, wherein the cushioning layer is integrally molded with the rear surface resin layer.

25. A heating apparatus of claim 23 or 24, wherein the cushioning layer is a heat insulator.

26. A heating apparatus of claim 8, wherein the rear surface resin layer is honeycombed.

27. A heating apparatus of claim 8, wherein the rear surface resin layer is provided with a hollow wherein a heat sensor is received.

28. A heating apparatus of claim 8, wherein the front surface resin layer facing a higher temperature portion of the heat source is made thick and the front surface resin layer facing a lower temperature portion of the heat source is made thin.

29. A room heating apparatus of any of claims 8 to 28, further comprising:

a human body detecting means for detecting presence of a person in a room; and a heat source control means for energizing the heat source only when the human body detecting means detects presence of a person.

30. A toilet heating apparatus of any of claims 8 to 28, further comprising a heat source control means for energizing the heat source in accordance with a control signal from outside a toilet.

31. A toilet heating apparatus of any of claims 8 to 28, further comprising a heat source control means for energizing the heat source only when an electric lamp in the toilet is switched on.

32. A toilet heating apparatus of any of claims 8 to 28, further comprising:

a human body detecting means for detecting presence of a person in a toilet; and a heat source control means for energizing the heat source only when the human body detecting means detects presence of a person.

33. A toilet heating apparatus of claim 32, wherein the heat source control means energizes the heat source a predetermined time after the human body detecting means detects presence of a person.

34. A toilet heating apparatus of claim 32, wherein the heat source control means energizes the heat source at time T-t after the human body detecting means detects presence of a person, where T is time between detection of presence of a person by the human body detecting means and seating of the person on a toilet seat, and t is time from energizing of the heat source to completion of temperature rise of the front surface resin layer to a predetermined level.

35. A toilet heating apparatus of claim 32, wherein the human body detecting means can detect distance between the human body detecting means and the person, and the heat source control means energizes the heat source when the distance between the human body detecting means and the person becomes a predetermined value.

36. A toilet heating apparatus of any of claims 30 to 35, wherein temperature coefficient of resistance of the heat source is positive.

37. A toilet heating apparatus of any of claims 30 to 35, wherein the heat source control means variably controls the electric power supply to the heat source.

38. A toilet heating apparatus of claim 37, wherein the heat source control means varies the electric power supply to the heat source stepwise.

39. A toilet heating apparatus of claim 37, wherein the heat source control means determines the electric power supply to the heat source by feedback control.

40. A toilet heating apparatus of claim 37, wherein the heat source control means determines the electric power supply to the heat source by learning control.

41. A toilet heating apparatus of any of claims 30 to 40, further comprising a seating detection means for detecting seating of a person on a toilet seat, wherein the heat source control means decreases the electric power supply to the heat source when the seating detection means detects seating of a person on the toilet seat.

* * * * *